US012318341B2

(12) United States Patent
Carballo et al.

(10) Patent No.: US 12,318,341 B2
(45) Date of Patent: *Jun. 3, 2025

(54) APPARATUS AND METHOD FOR REDUCTION OF NEUROLOGICAL MOVEMENT DISORDER SYMPTOMS USING WEARABLE DEVICE

(71) Applicant: Encora, Inc., Boston, MA (US)

(72) Inventors: Daniel Carballo, Boston, MA (US); Kyle Pina, Somerville, MA (US); Allison Davanzo, Green Cove Springs, FL (US); Trang Luu, Houston, TX (US)

(73) Assignee: Encora, Inc., Boston, MA (US)

( * ) Notice: Subject to any disclaimer, the term of this patent is extended or adjusted under 35 U.S.C. 154(b) by 845 days.

This patent is subject to a terminal disclaimer.

(21) Appl. No.: 17/494,347

(22) Filed: Oct. 5, 2021

(65) Prior Publication Data

US 2022/0062096 A1 Mar. 3, 2022

Related U.S. Application Data

(63) Continuation-in-part of application No. 17/063,363, filed on Oct. 5, 2020, now Pat. No. 11,701,293, which
(Continued)

(51) Int. Cl.
*A61H 23/00* (2006.01)
*A61B 5/00* (2006.01)
*A61B 5/11* (2006.01)

(52) U.S. Cl.
CPC .......... *A61H 23/004* (2013.01); *A61B 5/1101* (2013.01); *A61B 5/1104* (2013.01);
(Continued)

(58) Field of Classification Search
CPC .................. A61H 23/02; A61H 23/004; A61H 2201/1635; A61H 2201/165;
(Continued)

(56) References Cited

U.S. PATENT DOCUMENTS 3,972,038 A * 7/1976 Fletcher ............. A61B 5/02438
455/100
4,842,607 A 6/1989 Repperger et al.
(Continued)

FOREIGN PATENT DOCUMENTS

AU 2022203028 A1 5/2022
CA 2716407 C 4/2018
(Continued)

OTHER PUBLICATIONS

Beasley et al., "An Overview of Genetic Algorithms: Part 1, Fundamentals", University Computing, 15(2), pp. 58-69, 1993.
(Continued)

*Primary Examiner* — Timothy A Stanis
*Assistant Examiner* — Tyler A Raubenstraw
(74) *Attorney, Agent, or Firm* — Goodwin Procter LLP

(57) ABSTRACT

A multimodal wearable band uses mechanical vibrations to stimulate sensory neurons in the wrist or ankle to reduce the severity of tremors, rigidity, involuntary muscle contractions, and bradykinesia caused by neurological movement disorders and to free users from freezing induced by movement disorders. The device uses sensors to provide output used by a processing unit to determine a stimulation pattern for the user and to determine when stimulation is necessary, and then uses one or more transducers to correspondingly stimulate the user's neurological pathways to lessen the severity of the user's symptoms. The device can also be adapted to integrate with third party devices.

24 Claims, 16 Drawing Sheets

Related U.S. Application Data is a continuation-in-part of application No. 16/563,087, filed on Sep. 6, 2019, now Pat. No. 11,839,583.

(60) Provisional application No. 62/797,310, filed on Jan. 27, 2019, provisional application No. 62/729,977, filed on Sep. 11, 2018.

(52) U.S. Cl.
CPC .......... *A61B 5/4082* (2013.01); *A61B 5/7207* (2013.01); *A61B 5/7257* (2013.01); *A61B 5/7275* (2013.01); *A61H 2201/1635* (2013.01); *A61H 2201/165* (2013.01); *A61H 2201/5007* (2013.01); *A61H 2201/5058* (2013.01)

(58) Field of Classification Search
CPC .... A61H 2201/5007; A61H 2201/5058; A61H 23/00; A61B 5/681; A61B 5/1101; A61B 5/1104; A61B 5/4082; A61B 5/7207; A61B 5/7257; A61B 5/7275; A61B 5/1105

See application file for complete search history.

(56) References Cited

U.S. PATENT DOCUMENTS

| | | |
|---|---|---|
| 6,458,089 B1 | 10/2002 | Ziv-Av |
| 6,695,794 B2 | 2/2004 | Kaiser et al. |
| 6,730,049 B2 | 5/2004 | Kalvert |
| 6,959,215 B2 | 10/2005 | Gliner et al. |
| 7,349,739 B2 | 3/2008 | Harry et al. |
| 7,412,428 B2 | 8/2008 | Nugent |
| 7,481,782 B2 | 1/2009 | Scott et al. |
| 7,974,696 B1 | 7/2011 | DiLorenzo |
| 8,025,632 B2 | 9/2011 | Einarsson |
| 8,187,209 B1 | 5/2012 | Giuffrida |
| 8,190,251 B2 | 5/2012 | Molnar et al. |
| 8,463,378 B2 | 6/2013 | Tass |
| 8,644,938 B2 | 2/2014 | Craggs |
| 8,679,038 B1 | 3/2014 | Giuffrida |
| 8,744,587 B2 | 6/2014 | Miesel et al. |
| 8,762,065 B2 | 6/2014 | DiLorenzo |
| 9,072,891 B1 | 7/2015 | Rao |
| 9,211,417 B2 | 12/2015 | Heldman et al. |
| 9,238,142 B2 | 1/2016 | Heldman et al. |
| 9,282,928 B1 | 3/2016 | Giffrida |
| 9,289,603 B1* | 3/2016 | Giuffrida ........... A61N 1/36067 |
| 9,301,712 B2 | 4/2016 | McNames et al. |
| 9,452,287 B2 | 9/2016 | Rosenbluth et al. |
| 9,486,389 B2 | 11/2016 | Tass |
| 9,553,625 B2 | 1/2017 | Hatanaka et al. |
| 9,616,234 B2 | 4/2017 | Harry et al. |
| 9,802,041 B2 | 10/2017 | Wong et al. |
| 9,855,110 B2 | 1/2018 | Bitan et al. |
| 9,861,283 B1 | 1/2018 | Giuffrida |
| 9,877,679 B1 | 1/2018 | Giuffrida |
| 9,877,680 B1 | 1/2018 | Giuffrida et al. |
| 9,924,899 B2 | 3/2018 | Pracar et al. |
| 9,936,899 B2 | 4/2018 | Goldman |
| 9,968,784 B2 | 5/2018 | Skelton et al. |
| 9,973,614 B2 | 5/2018 | Thorn et al. |
| 9,974,478 B1 | 5/2018 | Brokaw et al. |
| 10,004,901 B2 | 6/2018 | Gliner |
| 10,016,606 B2 | 7/2018 | Afshar et al. |
| 10,085,689 B1 | 10/2018 | Giuffrida et al. |
| 10,092,754 B1 | 10/2018 | Heldman et al. |
| 10,173,060 B2 | 1/2019 | Wong et al. |
| 10,179,238 B2 | 1/2019 | Wong et al. |
| 10,195,097 B1* | 2/2019 | Cimo ................ A61H 1/00 |
| 10,251,611 B2* | 4/2019 | Marsh ................ A61B 5/7282 |
| 10,350,410 B2 | 7/2019 | Tass et al. |
| 10,365,614 B2 | 7/2019 | Von Allmen |
| 10,426,369 B2 | 10/2019 | Marks |
| 10,463,141 B2 | 11/2019 | Fitzgerald et al. |
| 10,478,626 B1 | 11/2019 | Heldman et al. |
| 10,485,478 B1 | 11/2019 | Mirov et al. |
| 10,549,093 B2 | 2/2020 | Wong et al. |
| 10,561,839 B2 | 2/2020 | Wong et al. |
| 10,603,482 B2 | 3/2020 | Hamner et al. |
| 10,625,074 B2 | 4/2020 | Rosenbluth et al. |
| 10,694,992 B1 | 6/2020 | Giuffrida et al. |
| 10,744,324 B2 | 8/2020 | Ó Laighin et al. |
| 10,750,946 B1 | 8/2020 | Giuffrida |
| 10,765,856 B2 | 9/2020 | Wong et al. |
| 10,786,200 B1 | 9/2020 | Giuffrida |
| 10,786,625 B1 | 9/2020 | Giuffrida et al. |
| 10,799,154 B2* | 10/2020 | Sarkar .................. A45B 3/00 |
| 10,814,130 B2 | 10/2020 | Wong et al. |
| 10,820,819 B2 | 11/2020 | Afshar et al. |
| 10,850,090 B2 | 12/2020 | Rosenbluth et al. |
| 10,881,856 B2 | 1/2021 | Heldman et al. |
| 10,905,879 B2 | 2/2021 | Wong et al. |
| 10,960,207 B2 | 3/2021 | Wong et al. |
| 10,966,652 B1 | 4/2021 | Giuffrida et al. |
| 10,974,049 B1 | 4/2021 | Heldman et al. |
| 11,000,229 B2 | 5/2021 | Leavitt et al. |
| 11,026,484 B2 | 6/2021 | Perkins et al. |
| 11,039,974 B2 | 6/2021 | Kodama et al. |
| 11,040,198 B1 | 6/2021 | Giuffrida et al. |
| 11,040,203 B1 | 6/2021 | Giuffrida et al. |
| 11,058,320 B2 | 7/2021 | Meftah et al. |
| 11,191,967 B1 | 12/2021 | Giuffrida et al. |
| 11,191,968 B1 | 12/2021 | Giuffrida et al. |
| 11,194,888 B1 | 12/2021 | Murphy et al. |
| 11,253,424 B2 | 2/2022 | Tass et al. |
| 11,311,235 B1 | 4/2022 | Giuffrida et al. |
| 11,331,480 B2 | 5/2022 | Hamner et al. |
| 11,344,722 B2 | 5/2022 | Wong et al. |
| 11,395,784 B2 | 7/2022 | Molina trejo |
| 11,504,038 B2* | 11/2022 | Howard ................. A61B 5/167 |
| 2002/0107556 A1 | 8/2002 | Mcloul et al. |
| 2003/0006357 A1 | 1/2003 | Kaiser et al. |
| 2004/0088025 A1 | 5/2004 | Gesotti |
| 2004/0254502 A1* | 12/2004 | McCamish .......... A61B 5/1101 |
| | | 600/587 |
| 2005/0234309 A1 | 10/2005 | Klapper |
| 2007/0004570 A1 | 1/2007 | Afanasenko et al. |
| 2007/0073361 A1 | 3/2007 | Goren et al. |
| 2007/0203435 A1 | 8/2007 | Novak |
| 2007/0203533 A1 | 8/2007 | Goren et al. |
| 2007/0250134 A1 | 10/2007 | Miesel et al. |
| 2007/0299374 A1* | 12/2007 | Gesotti .................. A61H 23/02 |
| | | 601/72 |
| 2008/0053253 A1 | 3/2008 | Moore et al. |
| 2008/0162088 A1 | 7/2008 | DeVaul et al. |
| 2009/0024062 A1 | 1/2009 | Einarsson |
| 2009/0024065 A1 | 1/2009 | Einarsson |
| 2009/0082691 A1 | 3/2009 | Denison et al. |
| 2009/0247910 A1 | 10/2009 | Klapper |
| 2010/0030119 A1 | 2/2010 | McNames et al. |
| 2010/0069798 A1 | 3/2010 | Cheng et al. |
| 2010/0145236 A1* | 6/2010 | Greenberg .......... G04G 21/025 |
| | | 600/595 |
| 2010/0234182 A1 | 9/2010 | Hoffman et al. |
| 2010/0249637 A1 | 9/2010 | Walter et al. |
| 2011/0054361 A1* | 3/2011 | Sakoda ................ A61B 5/4082 |
| | | 600/595 |
| 2011/0224530 A1* | 9/2011 | David ..................... A61B 5/021 |
| | | 600/388 |
| 2012/0172682 A1 | 7/2012 | Linderman et al. |
| 2013/0150697 A1* | 6/2013 | Imai ...................... A61B 5/296 |
| | | 600/372 |
| 2013/0214913 A1 | 8/2013 | Efrati |
| 2014/0005743 A1 | 1/2014 | Giuffrida et al. |
| 2014/0052275 A1 | 2/2014 | Pathak |
| 2014/0074179 A1 | 3/2014 | Heldman et al. |
| 2014/0074180 A1 | 3/2014 | Heldman et al. |
| 2014/0194781 A1 | 7/2014 | Einarsson |
| 2014/0336722 A1 | 11/2014 | Rocon De Lima et al. |
| 2014/0350436 A1 | 11/2014 | Nathan et al. |
| 2014/0375470 A1 | 12/2014 | Malveaux |
| 2015/0073310 A1* | 3/2015 | Pracar .................... A61B 5/74 |
| | | 600/595 |

(56) References Cited

U.S. PATENT DOCUMENTS

| | | | |
|---|---|---|---|
| 2015/0078140 A1* | 3/2015 | Riobo Aboy | G01S 19/42 368/11 |
| 2015/0164377 A1 | 6/2015 | Nathan et al. | |
| 2015/0182160 A1 | 7/2015 | Kim et al. | |
| 2015/0223731 A1 | 8/2015 | Sahin | |
| 2015/0272807 A1* | 10/2015 | Gupta | A61B 5/6824 601/33 |
| 2015/0335521 A1 | 11/2015 | Tedim Ramos Cruz et al. | |
| 2016/0113840 A1* | 4/2016 | Crunick | A61H 23/006 601/95 |
| 2016/0121110 A1* | 5/2016 | Kent | A61B 5/7282 607/45 |
| 2016/0140986 A1 | 5/2016 | Bowers et al. | |
| 2016/0287879 A1* | 10/2016 | Denison | A61N 1/36139 |
| 2016/0313174 A1 | 10/2016 | Lightstone | |
| 2016/0320915 A1 | 11/2016 | Williamson | |
| 2017/0007168 A1 | 1/2017 | Mirelman et al. | |
| 2017/0014625 A1 | 1/2017 | Rosenbluth et al. | |
| 2017/0156662 A1 | 6/2017 | Goodall et al. | |
| 2017/0188973 A1 | 7/2017 | Banet et al. | |
| 2017/0286658 A1* | 10/2017 | Zamfir | G01C 19/5776 |
| 2018/0000685 A1* | 1/2018 | Maloney | A61N 1/36031 |
| 2018/0021576 A1 | 1/2018 | Wong et al. | |
| 2018/0035943 A1 | 2/2018 | Shemesh et al. | |
| 2018/0036535 A1 | 2/2018 | Wong et al. | |
| 2018/0064344 A1 | 3/2018 | Nguyen | |
| 2018/0070840 A1* | 3/2018 | Cronin | A61B 5/7435 |
| 2018/0108241 A1 | 4/2018 | Wong et al. | |
| 2018/0140842 A1 | 5/2018 | OLaighin | |
| 2018/0169400 A1 | 6/2018 | Wong et al. | |
| 2018/0192946 A1 | 7/2018 | Adachi et al. | |
| 2018/0203482 A1 | 7/2018 | Nazzaro et al. | |
| 2018/0206774 A1 | 7/2018 | Huang | |
| 2018/0214694 A1* | 8/2018 | Parramon | A61N 1/36071 |
| 2018/0264263 A1* | 9/2018 | Rosenbluth | A61N 1/36031 |
| 2018/0266820 A1 | 9/2018 | de Panisse et al. | |
| 2018/0296154 A1 | 10/2018 | Johnson et al. | |
| 2018/0304082 A1 | 10/2018 | Afshar et al. | |
| 2018/0356890 A1* | 12/2018 | Zhang | G06F 3/014 |
| 2018/0361153 A1 | 12/2018 | Heldman et al. | |
| 2019/0001121 A1 | 1/2019 | Lara et al. | |
| 2019/0001129 A1 | 1/2019 | Rosenbluth et al. | |
| 2019/0038222 A1* | 2/2019 | Krimon | A61B 5/30 |
| 2019/0059733 A1 | 2/2019 | Nguyen | |
| 2019/0083007 A1* | 3/2019 | Jagannathan | A61B 5/6897 |
| 2019/0143098 A1 | 5/2019 | Kaplan et al. | |
| 2019/0183724 A1 | 6/2019 | Sifferlin | |
| 2019/0209022 A1 | 7/2019 | Sobol et al. | |
| 2019/0298605 A1 | 10/2019 | Rabolt et al. | |
| 2019/0365286 A1* | 12/2019 | Powers, III | A61B 5/6828 |
| 2020/0000373 A1* | 1/2020 | Agrawal | A61B 5/7405 |
| 2020/0054889 A1 | 2/2020 | Makansi | |
| 2020/0061378 A1 | 2/2020 | Ganguly et al. | |
| 2020/0093400 A1 | 3/2020 | Hamner et al. | |
| 2020/0163588 A1 | 5/2020 | Prevost et al. | |
| 2020/0179151 A1 | 6/2020 | Negretto et al. | |
| 2020/0179687 A1 | 6/2020 | Wong et al. | |
| 2020/0188210 A1* | 6/2020 | Molina Trejo | A61H 23/02 |
| 2020/0188223 A1 | 6/2020 | Nguyen | |
| 2020/0289814 A1 | 9/2020 | Hamner et al. | |
| 2020/0338358 A1 | 10/2020 | Makansi | |
| 2020/0410893 A1 | 12/2020 | Ridington | |
| 2021/0007874 A1 | 1/2021 | Galiana Bujanda et al. | |
| 2021/0030613 A1 | 2/2021 | Kodama et al. | |
| 2021/0045957 A1 | 2/2021 | Fuhrer | |
| 2021/0052883 A1 | 2/2021 | Wong et al. | |
| 2021/0085976 A1 | 3/2021 | Heldman et al. | |
| 2021/0100999 A1 | 4/2021 | Rosenbluth et al. | |
| 2021/0113152 A1 | 4/2021 | Turner | |
| 2021/0113834 A1 | 4/2021 | Wong et al. | |
| 2021/0186794 A1 | 6/2021 | Seim et al. | |
| 2021/0244316 A1 | 8/2021 | Khaled | |
| 2021/0244940 A1 | 8/2021 | Liberatore et al. | |
| 2021/0252278 A1 | 8/2021 | Hamner et al. | |
| 2021/0283400 A1 | 9/2021 | Hamner et al. | |
| 2021/0308460 A1 | 10/2021 | Wong et al. | |
| 2021/0330547 A1* | 10/2021 | Moaddeb | A61N 1/0452 |
| 2021/0330974 A1 | 10/2021 | Wong et al. | |
| 2021/0379374 A1 | 12/2021 | Hamner et al. | |
| 2021/0401664 A1 | 12/2021 | Tass | |
| 2021/0402172 A1 | 12/2021 | Ross et al. | |
| 2022/0001164 A1 | 1/2022 | Sharma et al. | |
| 2022/0007994 A1 | 1/2022 | Mattioli | |
| 2022/0008283 A1 | 1/2022 | Carballo et al. | |
| 2022/0008786 A1 | 1/2022 | Shah | |
| 2022/0054349 A1 | 2/2022 | Narula | |
| 2022/0062096 A1 | 3/2022 | Carballo et al. | |
| 2022/0165413 A1 | 5/2022 | Murphy et al. | |
| 2022/0176141 A1 | 6/2022 | Caparso et al. | |
| 2022/0233860 A1 | 7/2022 | Hamner et al. | |
| 2022/0266011 A1 | 8/2022 | Wong et al. | |
| 2022/0266012 A1 | 8/2022 | Hamner et al. | |
| 2022/0296894 A1 | 9/2022 | Jung | |

FOREIGN PATENT DOCUMENTS

| | | | | |
|---|---|---|---|---|
| CN | 204426918 U | 7/2015 | | |
| CN | 106178261 A | 12/2016 | | |
| CN | 206424425 U | 8/2017 | | |
| CN | 107307933 A | 11/2017 | | |
| EP | 3222207 A1 | 9/2017 | | |
| EP | 3479810 A1 * | 5/2019 | | A61F 5/013 |
| EP | 3498332 A1 | 6/2019 | | |
| EP | 3533392 A1 * | 9/2019 | | A61B 5/296 |
| JP | 2016-511651 A | 4/2016 | | |
| JP | 3226150 U | 4/2020 | | |
| WO | WO-2011119224 A2 * | 9/2011 | | A61B 5/04 |
| WO | WO-2011141734 A1 * | 11/2011 | | A61B 5/1101 |
| WO | 2014113813 A1 | 7/2014 | | |
| WO | 2019027512 A1 | 2/2019 | | |
| WO | 2019046180 A1 | 3/2019 | | |
| WO | 2020006048 A1 | 1/2020 | | |

OTHER PUBLICATIONS

Buki et al., "Vib-bracelet: A Passive Absorber for Attenuating Forearm Tremor", Med Biol Eng Comput, vol. 56, pp. 923-930, 2018.

Conrad et al., "Effects of Wrist Tendon Vibration on Arm Tracking in People Poststroke", J. Neurophysiol., 106(3), pp. 1480-1488, Jun. 2011.

Conrad et al., "Effect of Tendon Vibration on Hemiparetic Arm Stability in Unstable Workspaces", PLOS one, 10(12), pp. 1-18, Dec. 2015.

Deisenroth et al., "A Survey on Policy Search for Robotics", Foundations and Trends in Robotics, vol. 2(1-2) pp. 1-141, 2013.

Gebai et al., "Parkinson's Disease Treatment as Seen from a Mechanical Point of View", Advances in Parkinson's Disease, 5, pp. 97-106, Nov. 2016.

Hagbarth et al., "The Effects of Muscle Vibration in Spasticity, Rigidity, and Cerebellar Disorders", J. Neurol. Neurosurg. Pshyciat., vol. 31, pp. 207-213, 1968.

Lora-Millan et al., "Mechanical Vibration does not Systematically Reduce the Tremor in Essential Tremor Patients", vioRxiv 398875, http://dx.doi.org/10.1101/398875, pp. 1-35, Aug. 2018.

Macerollo et al., "Effect of Vibration on Motor Performance: A new intervention to improve bradykinesia in Parkinson's disease?", MDS Abstracts, 2 pages, Jun. 2016.

Turkistani, "Development of an Effective Portable and Flexible Glove for Hand Tremor Suppression", Master's Theses, 65 pages, Spring, 2017.

European Patent Office; International Search Report and Written Opinion dated Jan. 27, 2022 for PCT Application No. PCT/US2021/053561 (19 pages).

Office Action for Japanese Patent Application No. 2023-521086, mailed Aug. 30, 2024.

International Search Report and Written Opinion for International Patent Application No. PCT/US2024/041732, mailed Nov. 5, 2024.

International Preliminary Report on Patentability for International Patent Application No. PCT/US2021/053561, mailed Apr. 20, 2023.

(56) References Cited

OTHER PUBLICATIONS

Office Action for Japanese Patent Application No. 2023-521086, mailed Feb. 20, 2024.
Examination Report for Australian Patent Application No. 2021358730, mailed May 13, 2024.
Examination Report for European Patent Application No. 21801735.8, mailed Feb. 11, 2025.
Examination Report for Australian Patent Application No. 2021358730, mailed Feb. 14, 2025.
Notice of Allowance for U.S. Appl. No. 18/189,397, mailed Feb. 13, 2025.

* cited by examiner

WITHOUT DEVICE     WITH DEVICE

APPARATUS AND METHOD FOR REDUCTION OF NEUROLOGICAL MOVEMENT DISORDER SYMPTOMS USING WEARABLE DEVICE

PRIORITY

This patent application is a continuation-in-part of U.S. patent application Ser. No. 17/063,363, filed Oct. 5, 2020, which is a continuation-in-part of U.S. patent application Ser. No. 16/563,087, filed Sep. 6, 2019, which claims the benefit of U.S. provisional patent application Ser. No. 62/729,977, filed on Sep. 11, 2018, and U.S. provisional patent application Ser. No. 62/797,310, filed on Jan. 27, 2019. These applications are hereby incorporated, in their entirety, by reference.

TECHNICAL FIELD

The present invention relates to wearable medical devices and in particular to wearable medical devices that mitigate symptoms of neurological movement disorders.

BACKGROUND ART

There are a number of neurological movement disorders which exhibit a range of somewhat similar symptoms, examples of which follow. Essential tremor is characterized by tremor of the extremities. Parkinson's Disease (PD) can cause tremor, rigidity, bradykinesia, and temporary freezing or inability to begin a motion. Restless Leg Syndrome does not cause a tremor; however, it causes a strong compulsion to move and shake the patient's legs. Tremor can also be present as a side effect of certain medications.

There are approximately 10 million people living with Parkinson's Disease (PD) in the world today, and over 70% of these patients experience tremors—the involuntary trembling or shaking of the extremities. Other symptoms of PD include stiffness or rigidity of the muscles, bradykinesia (defined as slowness of movement), and freezing (defined as the temporary, involuntary inability to move).

Parkinson's Disease has no cure. Treatments at the moment consist of medications to address patients' symptoms, though these do not reverse the effects of the disease. Patients often take a variety of medications at different doses and different times of day to manage symptoms. PD medications are most often dopaminergic, either supplying or mimicking the effects of dopamine to replenish the depleted dopamine state caused by the disease.

Surgical procedures can be prescribed for patients who have exhausted other medical treatment options. The first method of surgical treatment is Deep Brain Stimulation (DBS). In this procedure, electrodes are inserted into the brain, and then an impulse generator battery is implanted under the collar bone or in the abdomen. The patient uses a controller to power the device on or off, as needed, to help control tremors. DBS can be effective for both Parkinson's disease and essential tremor, but this procedure is invasive and expensive.

The second surgical procedure available for Parkinson's patients is Duopa therapy. Duopa therapy requires a small hole (a stoma) to be surgically made in the stomach to place a tube in the intestine. Duopa, which is similar to normal PD medications taken through pills, is then pumped directly into the intestine, which improves absorption and reduces off-times of medications taken by pill.

A similar disorder, called essential tremor, is often misdiagnosed as Parkinson's but has an even higher incidence rate with an estimated 100 million cases worldwide. These tremors often occur during intentional movement and can get bad enough that patients no longer have the ability to cut their food, tie their shoes, or sign their name. Essential tremor medications can include beta blockers and anti-seizure medications. These medications are known to cause fatigue, heart problems, and nausea.

Multiple Sclerosis (MS) is an inflammatory autoimmune disease of the central nervous system, which affects an estimated 2.8 million people globally. Motor symptoms include weakness or fatigue, gait difficulties, stiffness or spasticity, and tremor. Most people experience what is called a "relapsing-remitting" disease course, which involves periods of new symptoms or relapses, followed by periods of recovery. As the disease progresses, symptom occurrence may take on a regular pattern, after which the disease is classified as "secondary-progressive". Some MS patients may experience a gradual onset and progression without any relapse-remittance, which is classified as "primary-progressive". There is no cure for MS, and treatment typically focuses on recovery from relapse attacks using physical therapy and medication. Disease-modifying medications reduce the occurrence of relapses, but will not aid symptom reduction during a relapse.

Restless Leg Syndrome (RLS) affects roughly 10% of the population in the United States. RLS can also be a side effect of primary Parkinson's Disease. RLS is characterized by unpleasant tingling sensations in the patient's legs. These sensations occur when the legs are still and are alleviated when the legs are in motion. As a result, RLS patients are compelled to move or shake their legs. This is particularly detrimental to the quality of patients' sleep as they are unable to remain still.

RLS is commonly treated by dietary changes, medications, and/or physical therapy. Dietary changes can include eliminating caffeine, alcohol, and tobacco. Medications prescribed for RLS can include the same type of medications prescribed for Parkinson's Disease (such as dopamine agonists and carbidopa-levodopa) and benzodiazepines (such as lorazepam, Xanax, Valium, and Ativan). Physical therapy for RLS can include massaging the legs or electrical or vibrational stimulation.

One example of a device that uses vibration to treat RLS is described in "Systems, devices, and methods for treating restless leg syndrome and periodic limb movement disorder," Walter, T. J., & Marar, U. (2010), U.S. Patent Application Publication No. US20100249637A1. This device is a lower leg sleeve with sensors and actuators, but it does not store or transmit data, nor does it address any of the other symptoms common to neurological movement disorders.

There are a number of pharmaceutical avenues for the management of neurological movement disorders that function by promoting dopamine, a chemical produced by the brain which helps control body movement. This chemical is lacking in the brains of patients with diseases such as Parkinson's disease. Pharmaceutical treatment for Parkinson's disease is expensive, costing users thousands of dollars annually; ineffective, wearing off quickly; and thought to actually accelerate neurodegeneration.

There also exists an injection-based Botox treatment for more severe tremors which costs tens of thousands of dollars annually and works by killing the nerves responsible for the tremors. This is effective in reducing the tremors, but the death of the nerves also causes a significant decrease in mobility. Additionally, this treatment is only available at very specialized treatment centers and therefore is not an option for the vast majority of patients.

There are a number of devices that attempt to control unwanted movement using surface-based treatment, but none have proven to be completely non-invasive and effective. Many have settled on electrical stimulation as their chosen mode of neurostimulation for the relief of unwanted movement. This can involve various equipment and inconvenient procedures such as gel pads or electrodes that require shaving for proper attachment. See "Closed-loop feedback-driven neuromodulation," DiLorenzo, D. J. (2014), U.S. Pat. No. 8,762,065B2. These devices only work after the electrical treatment is concluded, and the effects have not been shown to last for extended periods of time, leading to the assumption that many of these inconvenient treatments must be administered throughout the day to maintain tremor reduction. See "Devices and methods for controlling tremor," Rosenbluth, K. H., Delp, S. L., Paderi, J., Rajasekhar, V., & Altman, T. (2016), U.S. Pat. No. 9,452,287B2; "Systems for peripheral nerve stimulation to treat tremor," Wong, S. H., Rosenbluth, K. H., Hamner, S., Chidester, P., Delp, S. L., Sanger, T. D., & Klein, D. (2017), U.S. Pat. No. 9,802,041B2; "Methods for peripheral nerve stimulation", Wong, S. H., Rosenbluth, K. H., Hamner, S., Chidester, P., Delp, S. L., Sanger, T. D., & Klein, D. (2020), U.S. Pat. No. 10,905,879B2. The aforementioned treatment poses significant risk for patients with pacemakers, and has also been found to cause skin irritation. It provides benefit only for tremor and does not provide relief from other symptoms of neurological movement disorders, such as bradykinesia, freezing of gait, dystonia, dyskinesia, or involuntary or compulsive rhythmic movement.

Perhaps the most relevant studies have emerged in the last few years and demonstrate that using vibration may improve motor performance. It seems that there is much variation in efficacy, which depends on the frequency of vibration, as well as the patient's condition. Macerollo et al. demonstrated that 80 Hz peripheral tactile vibration may result in less slowing and a decrease in repetitive hand movement in "Effect of Vibration on Motor Performance: A new Intervention to Improve Bradykinesia in Parkinson's Disease?", Macerollo A, et al., (2016), Neurology April 2016, 86 (16 Supplement) P5.366. For post-stroke patients, 70 Hz has proven effective. This is demonstrated by Conrad M O, et al., in two separate papers: "Effects of wrist tendon vibration on arm tracking in people poststroke," Conrad M O, Scheidt R A, Schmit B D (2011), J Neurophysiol, 2011; 106 (3): 1480-8; and "Effect of Tendon Vibration on Hemiparetic Arm Stability in Unstable Workspaces," Conrad M O, Gadhoke B, Scheidt R A, Schmit B D (2015), PLOS ONE 10 (12): e0144377. Even paretic muscles are proven to respond to frequencies between 150 and 160 Hz, and the effects of such vibration are seen in a lasting reduction in weakness and spasticity in the treated muscles. See "The effects of muscle vibration in spasticity, rigidity, and cerebellar disorders," Hagbarth, K. E., & Eklund, G. (1968), Journal of neurology, neurosurgery, and psychiatry, 31 (3), 207-13. Vibration may even have positive effects on rigidity or stiffness by increasing relaxation using vibrotactile stimulation, as shown in three separate studies: "Joint mobility changes due to low frequency vibration and stretching exercise," Atha J, Wheatley D W, British Journal of Sports Medicine 1976; 10:26-34; "Vibration Effects on Three Measures of Relaxation," Johnson, M. D., Hensel, C. L., & Matheson, D. W. (1982), Perceptual and Motor Skills, 54 (3_suppl), 1071-1076; and "Relaxation measured by EMG as a function of vibrotactile stimulation," Matheson, D. W., Edelson, R., Hiatrides, D. et al. (1976), Biofeedback and Self-Regulation 1, 285-292. There exists one device which provides haptic signals around a user's wrist using actuators positioned along a band. These actuators slide along the band to change location relative to one another in order to provide signals in the correct location. See "Wearable device," Zhang, Haiyan, Helmes, John Franciscus Marie, Villar, Nicolas (2018), U.S. Patent Application Publication No. US20180356890A1.

Therefore, there is a need for a device that non-invasively, reliably, and affordably relieves symptoms of neurological movement disorders.

SUMMARY OF THE EMBODIMENTS

In accordance with one embodiment of the invention, a wearable device is provided for modulating a set of movement disorder symptoms of a subject. The device includes a housing and an attachment system, configured to be attached to a body part of a subject. The device further includes a set of body part sensors to provide a set of sensor outputs related to movement of the body part, and a set of mechanical transducers, coupled to the attachment system, configured to provide a set of mechanical outputs to the body part. The device also includes a processing unit having (i) an input operationally coupled to sensor outputs to receive body part movement data; (ii) noise filtration processing to remove, from the body part movement data, noise unrelated to the movement disorder symptoms so as to produce a filtered movement signal; (iii) feature extraction processing of the filtered movement signal to characterize features of the filtered movement signal so as to produce a characterized filtered movement signal; and (iv) stimulation processing of the characterized filtered movement signal to produce a stimulation signal output, such output being operationally coupled to the set of mechanical transducers, causing the transducers to provide, to the body part, mechanical stimulation that mitigates the set of movement disorder symptoms.

Alternatively or additionally, the processing unit is further configured to provide active noise cancellation by (a) transforming body part movement data in the time domain into frequency domain data, (b) using the frequency domain data to determine a fundamental frequency of the movement disorder symptoms, (c) generating the stimulation signal output, based on the body part movement data, having a desired phase shift, relative to a phase of the body part movement data at the fundamental frequency.

In other embodiments, the processing unit is further configured to provide, at the simulation signal output, a train of stimulation signals, each signal in the train having a distinct set of parameters associated with mitigating the set of movement disorder symptoms and wherein the feature extraction processing includes determining displacement or power data associated with the movement of the body part, and the processing unit is also configured to use the displacement or power data to determine which stimulation signal in the train has the greatest mitigation effect. In preferred embodiments, the processing unit is further configured to select the stimulation signal determined to have the greatest mitigation effect for continuous output to the transducers.

Optionally, the set of movement disorder symptoms is selected from the group consisting of tremor, rigidity, bradykinesia, dyskinesia, compulsion to move, and combinations thereof. Optionally, the processing unit is further configured to detect a freezing gait of a patient with Parkinson's Disease. Alternatively or additionally, the processing unit is further configured to control the set of mechanical transducers so as to mitigate the freezing gait of the patient with Parkinson's Disease by controlling the set of mechanical transducers. Optionally, the processing unit is configured to operate in two modes, a first mode in which it is configured to monitor patient movements passively to detect a movement disorder symptom above a threshold and a second mode in which, following detection of such a movement disorder symptom, the processor is configured to enter into active mitigation of the movement disorder symptom.

Optionally, the attachment system includes a wristband, and the set of mechanical transducers are distributed throughout the circumference of the wristband. Optionally, the device is operated by a button on a face of the device, and the button is configured on the face to allow for ease of use by a patient whose fine motor control is affected by a neurological movement disorder. Optionally, the wristband is configured with a hook-and-loop fastener, such that the wristband can be fastened with a single hand for ease of use by those whose fine motor control is affected by a neurological movement disorder. Optionally, the wristband is configured to be expandable via elastic deformation for ease of use by those whose fine motor control is affected by a neurological movement disorder. Optionally, the device further includes a battery, disposed in the housing, and a magnetic connector coupled to the battery and mounted in the housing for coupling to a mating connector for an external charger, so that the battery can be conveniently configured for charging by a patient lacking fine motor control.

Optionally, the processing unit is further configured to store the body part movement data in memory coupled to the processing unit.

Optionally, the active noise cancellation processor is configured to transform the sensor output into the frequency data by applying a Fourier Transform to the sensor output. Alternatively or additionally, the active noise cancellation processor is configured to: (i) select the fundamental frequency by applying an argmax function to the transformed sensor output and (ii) use a bandpass filter to remove, from the stimulation signal, a set of frequency data outside a specified range associated with the fundamental frequency.

Optionally, the set of body part sensors includes an inertial motion unit (IMU) configured to calculate data representing the body part's acceleration, and the active noise cancellation processor is further configured to: transform the body part's acceleration data to the frequency data by applying a Fourier Transform; extract peak frequencies of the body part's acceleration data from the frequency data; select a window size of the body part's acceleration data based on the peak frequencies; and capture a portion of the sensor output based on the selected window size and invert the captured portion to generate the stimulation signal. Alternatively or additionally, the active noise cancellation processor is configured to select the window size by inverting a lowest of the peak frequencies and converting the inverted lowest of the peak frequencies into a time domain. Optionally or additionally, the active noise cancellation processor is configured to set the window size to a fixed value.

In accordance with embodiments of the present invention, a method is provided for mitigating a set of movement disorder symptoms of a subject. The method includes sensing movement of a body part of the subject to provide a set of sensor outputs related to movement of the body part. The method also includes processing the sensor outputs to produce a stimulation signal for mitigating the set of movement disorder symptoms. The processing includes filtering the sensor outputs to remove noise unrelated to the movement disorder symptoms so as to produce a filtered signal.

Optionally, the processing also includes actively processing the filtered signal to (a) transform the sensor outputs into frequency data, (b) use the frequency data to determine a fundamental frequency of the movement disorder symptoms, (c) generate the stimulation signal by processing the sensor outputs based on the fundamental frequency; and (d) apply, to the stimulation signal, a time delay calculated based on the fundamental frequency. The method further includes inputting the stimulation signal to a set of mechanical transducers coupled to the body part so as to mitigate the set of movement disorder symptoms.

Alternatively or additionally, the processing unit includes a fixed frequency processor, configured to (a) input a set of stimulation signals in succession to the set of mechanical transducers, wherein the set of stimulation signals vary in frequency, (b) transform the sensor outputs into displacement or power data, (c) use the displacement or power data to determine which stimulation signal results in the lowest displacement, and (d) transmit said stimulation signal to the set of mechanical transducers. Optionally, the processing unit is configured to take input from a user, and use that input to control the stimulation signal.

Optionally, the set of movement disorder symptoms is selected from the group consisting of tremor, rigidity, bradykinesia, dyskinesia, compulsion to move, and combinations thereof. Optionally, sensing movement of a body part includes operating in two modes, a first mode that monitors patent movements passively to detect a movement disorder symptom above a threshold and a second mode that, following detection of such a movement disorder symptom, enters into active mitigation of the movement disorder symptom. Optionally, actively processing the filtered signal to transform the sensor outputs into frequency data includes applying a Fourier Transform to the sensor output. Alternatively or additionally, actively processing the filtered signal to transform the sensor outputs into frequency data includes: (i) selecting the fundamental frequency by applying an argmax function to the transformed sensor output and (ii) using a bandpass filter to remove, from the stimulation signal, a set of frequency data outside a specified range associated with the fundamental frequency.

Optionally, processing the sensor outputs to produce the stimulation signal further include calculating data representing the body part's acceleration; transforming body part's acceleration data to the frequency data by applying a Fourier Transform; extracting peak frequencies of the body part's acceleration data from the frequency data, selecting a window size of the body part's acceleration data based on the peak frequencies; and capturing a portion of the sensor output based on the selected window size and inverting the captured portion to generate the stimulation signal. Alternatively or additionally, selecting the window size includes inverting a lowest of the peak frequencies and converting the inverted lowest of the peak frequencies into a time domain. Alternatively or additionally, selecting the window size includes setting the window size to a fixed value.

In accordance with other embodiments of the invention, a method is provided for mitigating a set of movement disorder symptoms of a subject, the method including the steps of monitoring sensor outputs of sensors configured to sense movement of a body part of the subject to provide a set of sensor outputs related to movement of the body part, processing the sensor outputs to produce a stimulation signal for mitigating the set of movement disorder symptoms by filtering the sensor outputs to remove noise unrelated to the movement disorder symptoms so as to produce a filtered signal, using a fixed frequency processor configured to (a) input a set of stimulation signals in succession to the set of mechanical transducers, wherein the set of stimulation signals vary in frequency, (b) transform the sensor outputs into displacement or power data, (c) output the stimulation signal resulting in the greatest mitigation effect.

In some embodiments, the processor is further configured to use displacement or power data to select the stimulation signal resulting in the greatest mitigation effect. In some embodiments, the processor is further configured to receive input from a user to select the stimulation signal resulting in the greatest mitigation effect.

In accordance with some embodiments, a method is provided of diagnosing a movement disorder in a patient according to the steps of:
(1) using a processor to provide, to a set of mechanical transducers, an output of a train of stimulation signals, successively varying in stimulation parameters, in order to induce symptoms of a movement disorder;
(2) receiving body part movement data, related to the movement of the body part, from a set of body part sensors;
(3) filtering the body part movement data to remove noise unrelated to the movement disorder symptoms so as to produce a filtered signal; and
(4) actively processing the filtered signal to (a) transform the sensor outputs into frequency data, (b) use the frequency data to determine a fundamental frequency of the movement of the body part; and
(5) further processing the frequency data to determine a probability that the subject is suffering from the movement disorder.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1:
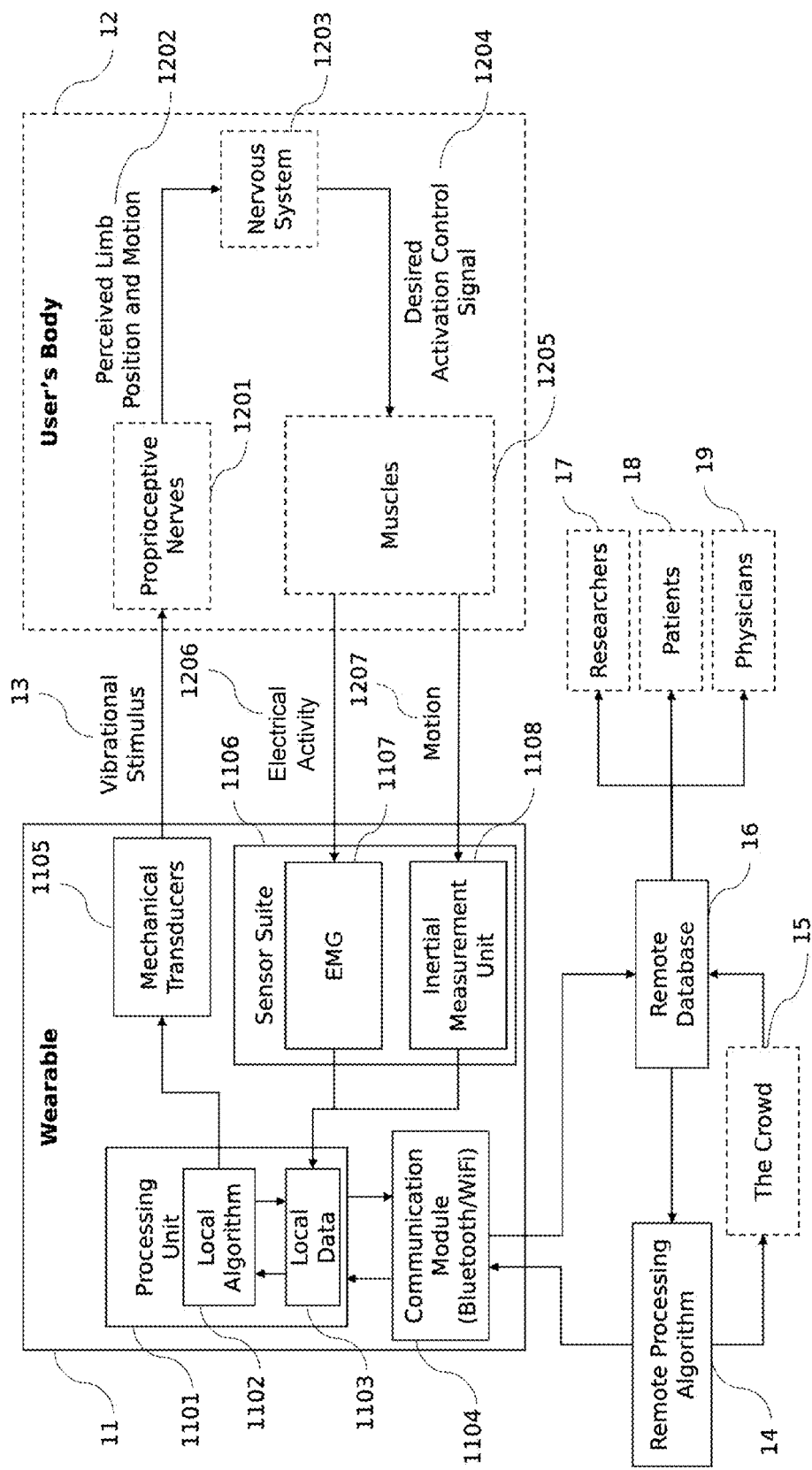
FIG. 1 illustrates a system for mitigating movement disorder in accordance with an embodiment of the present invention.

Definitions. As used in this description and the accompanying claims, the following terms shall have the meanings indicated, unless the context otherwise requires:

A "set" includes at least one member.

A "body part" is a part of a human body, such as a limb (examples of which include an arm, a leg, an ankle, and a wrist) or the neck.

A "body part sensor" is a sensor responsive to a parameter, associated with a body part, the parameter selected from the group consisting of force, motion, position, EMG signal directed to a set of muscles of the body part and combinations thereof.

A "mechanical transducer" is a device having an electrical input and a mechanical output configured to provide physical stimulation to a subject.

A "movement disorder sensor" is a sensor that is configured to provide a measurement associated with a neurological movement disorder.

An "attachment system" is a system or a device having a means to mechanically affix component subsystems to the user's person.

A "housing" is a primary enclosed casing which contains one or more component subsystems.

A "band" is a flexible segment of material which encircles a body part or portion of a body part for the purpose of affixation thereto and which material may also house one or more component subsystems.

The term "vibrational stimulus" refers to a vibration or series of vibrations produced by a vibration motor or group of vibration motors embedded in the device. These vibrations are used to stimulate a response from the targeted proprioceptors in the user's body.

The term "stimulation pattern" refers to a vibrational stimulus which is characterized by a number of parameters including frequency, amplitude, and waveform. A "stimulation pattern" can also refer to a longer time scale behavior over which the above-mentioned parameters evolve over time.

The term "proprioception" refers to the sense of the position of one's own limbs or body parts and the intensity of force being applied through that body part. A proprioceptor is a sensory neuron which is used for proprioception. There are two types of proprioceptors: "muscle spindles" which are located in the muscle and the "Golgi tendon organs" which are located in the tendons.

The term "neurological movement disorder" refers to any of the neurological conditions that cause abnormally increased or decreased movements which may be voluntary or involuntary. These include but are not limited to: Ataxia, cervical dystonia, chorea, dystonia, functional movement disorder, Huntington's disease, multiple system atrophy (MSA), paresis, hemiparesis, quadriparesis, post-stroke movement disorders, myoclonus, Parkinson's disease (PD), Parkinsonism, drug induced Parkinsonism (DIP), progressive supranuclear palsy (PSP), restless legs syndrome (RLS), tardive dyskinesia, Tourette syndrome, spasticity, rigidity, bradykinesia, tremor, essential tremor (ET), alcohol or drug withdrawal induced tremor, drug induced tremor, psychogenic tremor, rest tremor, action tremor, cerebellar lesion, rubral tremor, isometric tremor, task-specific tremor, orthostatic tremor, intention tremor, postural tremor, periodic limb movement disorder, and Wilson's disease.

The term "training period" refers to a period or phase of the device's operation during which the device is conducting experimentation or collecting and analyzing data for the purpose of deducing the optimal stimulation pattern.

A "computer process" is the performance of a described function in a computer system using computer hardware (such as a processor, field-programmable gate array or other electronic combinatorial logic, or similar device), which may be operating under control of software or firmware or a combination of any of these or operating outside control of any of the foregoing. All or part of the described function may be performed by active or passive electronic components, such as transistors or resistors. In using the term "computer process" we do not necessarily require a schedulable entity, or operation of a computer program or a part thereof, although, in some embodiments, a computer process may be implemented by such a schedulable entity, or operation of a computer program or a part thereof. Furthermore, unless the context otherwise requires, a "process" may be implemented using more than one processor or more than one (single- or multi-processor) computer.

Wearable Treatment Device. The present invention is directed generally towards wearable medical devices and in particular towards the mitigation of tremors, rigidity, bradykinesia, involuntary rhythmic movements, and freezing associated with neurological movement disorders through mechanical vibrational stimulation of the tendon bundles in the wrist and autonomous sensing, feedback, and adjustment. There are also a number of considerations taken into the embodiment of the device which facilitate ease of use by the disabled populations for whom the invention is intended, including integration with 3rd party devices.

Embodiments of the present invention include systems and methods of treating symptoms of neurological movement disorders by stimulating proprioceptors. In some embodiments, the systems are wearable devices. In some embodiments, the systems and methods can be used for any neurological movement disorder, including but not limited to Parkinson's Disease, Essential Tremor, post-stroke movement disorders, or restless leg syndrome. In some embodiment, the symptoms treated include tremor, rigidity, bradykinesia, stiffness, hemiparesis, and freezing. In some embodiments, the symptoms treated include muscle contraction caused by dystonia. In some embodiments, the symptoms treated include the inability to locate one's limbs in space. In some embodiments, the proprioceptors targeted for stimulation are located in the wrist. In some embodiments, the proprioceptors targeted for stimulation are located in the ankle. In some embodiments, the proprioceptors targeted for stimulation are located in the neck.

In some embodiments, the systems provide stimulus to the proprioceptive nerves (proprioceptors) for reducing symptoms by the use of vibration motors positioned around the surface of the wrist. In some embodiments, the systems cycle through frequency patterns and waveforms of stimulation to find the pattern that results in the greatest reduction of movement disorder symptoms. In some embodiments, the systems use random white-noise subthreshold stimulation in order to leverage the effect of sensory stochastic resonance. In some embodiments, the systems are coupled to one or more sensors that measure the user's tremor for each of a set of possible stimulation patterns, and the systems assign the pattern of stimulation that relates to the biggest measured decrease in tremor amplitude of that user relative to the tremor exhibited in the absence of stimulation In some embodiments, the device finds (learns) the optimal stimulation parameters for use in reducing the symptoms by using sensor-based optimization, including but not limited to model free reinforcement learning, genetic algorithms, Q-learning. These parameters can include any quantities used to define a stimulation waveform such as frequency, amplitude, phase, duty cycle, etc. In some embodiments, these learned parameters also describe the longer time scale behavior of the stimulation pattern evolving over time. In some embodiments, the device determines the optimal stimulation as the weighted average of the optimal stimulations for each of the independent symptoms observed where the weights are proportional to the symptom severity relative to the other observed symptoms. For example, if the patient experienced tremors and rigidity, and the severity of the tremors was double that of the rigidity, the output stimulation would be two times the optimal tremor reducing pattern superposed with one times the optimal rigidity reducing pattern. In some embodiments, the device senses all of the active symptoms and elects to reduce only the symptom with the worst severity. In some embodiments, the device, via sensors, measures the shaking due to RLS of the user and assigns the pattern that relates to the biggest decrease in shaking amplitude of that user where the amplitude is that of the sensor signal and the difference is defined relative to the amplitude observed in the absence of stimulation from the device.

In some embodiments, the sensors coupled to the device are a combination of accelerometers, gyroscopes, IMUs, or other motion-based sensors. In some embodiments, the sensors coupled to the device also include electromyography (EMG) sensors to monitor muscle activation in order to sense tremor severity, rigidity, or movement due to RLS. In some embodiments, the device collects data on the characteristics of the user's symptoms, such as motion amplitude and frequency or muscle activity with sensors contained in the device such as an accelerometer, pressure sensors, force sensors, gyroscope, Inertial Measurement Unit (IMU), or electromyography (EMG) sensors. In some embodiments, the above-mentioned data would be stored through storage components contained within the device. In some embodiments, the above-mentioned data is regularly consolidated for the purpose of larger scale data analysis through a wired or wireless transfer of data to a larger storage location not on the device.

In some embodiments, the actuators are resistive heating elements rather than vibration motors. In some embodiments, the actuators are vibration motors. In some embodiments, the actuators are electromagnets-. In some embodiments, the actuators are electropermanent magnets. In some embodiments, the actuators are piezoelectric actuators. In some embodiments, the actuators are voice coil vibration motors. In some embodiments, the actuators are rotating eccentric mass vibration motors. In some embodiments, the device is an accessory band to a third-party smartwatch or other wearable computing device. In some embodiments, the device can connect wirelessly (for example via Bluetooth) to the user's smartphone. In some embodiments, the device can be configured to provide contextualized data about the user's condition. For example, the system can correlate symptom onset or degree with time of day, activity level, medication, diet, other symptoms, etc. In some embodiments, this can be accomplished by transmitting extracted sensor signal features to the user's smartphone. An accompanying smartphone application can periodically prompt the user to input other information like activity level, diet, and medication. The application then logs this data with time matched symptom sensor signal features to be reviewed by the user and/or their physician.

In some embodiments, the device can be started by passive sensing of the onset of symptoms such as the on/off phenomenon of Parkinson's patients taking L-dopa. In some embodiments, this can be accomplished by continuously reading sensor data, even while in the "off" state, and then switching to the "on" state when one of the sensor data features, such as amplitude, surpasses a preset threshold value. In some embodiments, the device can be used to amplify an existing but subtle tremor for the purpose of early diagnosis. In some embodiments, this can be accomplished by manually testing a set of stimulation patterns until the tremor is apparent, either visually or as detected by an extracted feature of the sensor data surpassing some preset threshold. In some embodiments, this can be accomplished autonomously by inverting the stimulation selection algorithm heuristic such that it converges to the stimulation pattern which maximizes tremor amplitude as measured by the symptom sensor relative to the tremor amplitude measured in the absence of stimulation from the device.

FIG. 1 illustrates a system for mitigating movement disorder in accordance with an embodiment of the present invention. The wearable device 11 and user's body 12 act as a system with inputs and outputs which may be manipulated to change the desired outcome of the system. The wearable device 11 interfaces with a user's body 12. The user's body 12 includes proprioceptive nerves 1201, perceived limb position and motion 1202, a nervous system 1203, desired activation control signal 1204, and muscles 1205. The muscles 1205 output electrical activity 1206, which is detected by the EMG sensor 1107 in the wearable's sensor suite 1106, and collected as local data 1103. The muscles 1205 also output motion 1207, which is detected by the inertial measurement unit (IMU) 1108. The IMU 1108 measures the body's specific force, angular rate, and orientation, and reports to the processing unit 1101. The processing unit 1101 receives the local data 1103 and executes a local algorithm 1102. Using the local data 1103, the processing unit 110, based on results of the local algorithm 1102, instructs the mechanical transducers 1105 to deliver a specific vibrational stimulus 13. The proprioceptive nerves 1201 detect the vibrational stimulus 13 and send the perceived limb position and motion 1202 to the nervous system 1203. Based on that signal, the nervous system 1203 sends a desired activation control signal 1204 to activate the muscles 1205 in a way that either alters or perpetuates their electrical activity 1206 and motion 1207. The local data 1103 collected by the sensor suite 1106 continues to be processed by the local algorithm 1102, and continues to affect the output of the mechanical transducers 1105. The local data 1103 is also transmitted via the communication module 1104 to a remote processing algorithm 14, and to a remote database 16 for long-term data storage and access by researcher 17, patients 18, or physicians 19. The remote database 16 also receives data from the greater population, or the crowd 15, and sends this data to the remote processing algorithm 14. The remote processing algorithm 14 analyzes the data and returns the results of the analysis both to the processing unit 1101, via the communication module 1104, and also to the crowd 15. In this way, data from the crowd 15 may influence the way that the local algorithm 1102 operates.

In some embodiments, the processing unit 1101 is configured to operate in two modes, a first mode in which it is configured to monitor patient movements passively to detect a movement disorder above a threshold and a second mode in which, following detection of such a movement disorder, the processor is configured to enter into active mitigation of the movement disorder. In some embodiments, processing unit 1101 enters into active mitigation by passive sensing of the onset of symptoms, such as the on/off phenomenon of Parkinson's patients taking L-dopa. In some embodiments, such passive sensing is performed by continuously reading sensor data, even while in the "off" state, and then switching to the "on" state when one of the sensor data features, such as amplitude, surpasses a preset threshold value.

Figure 2:
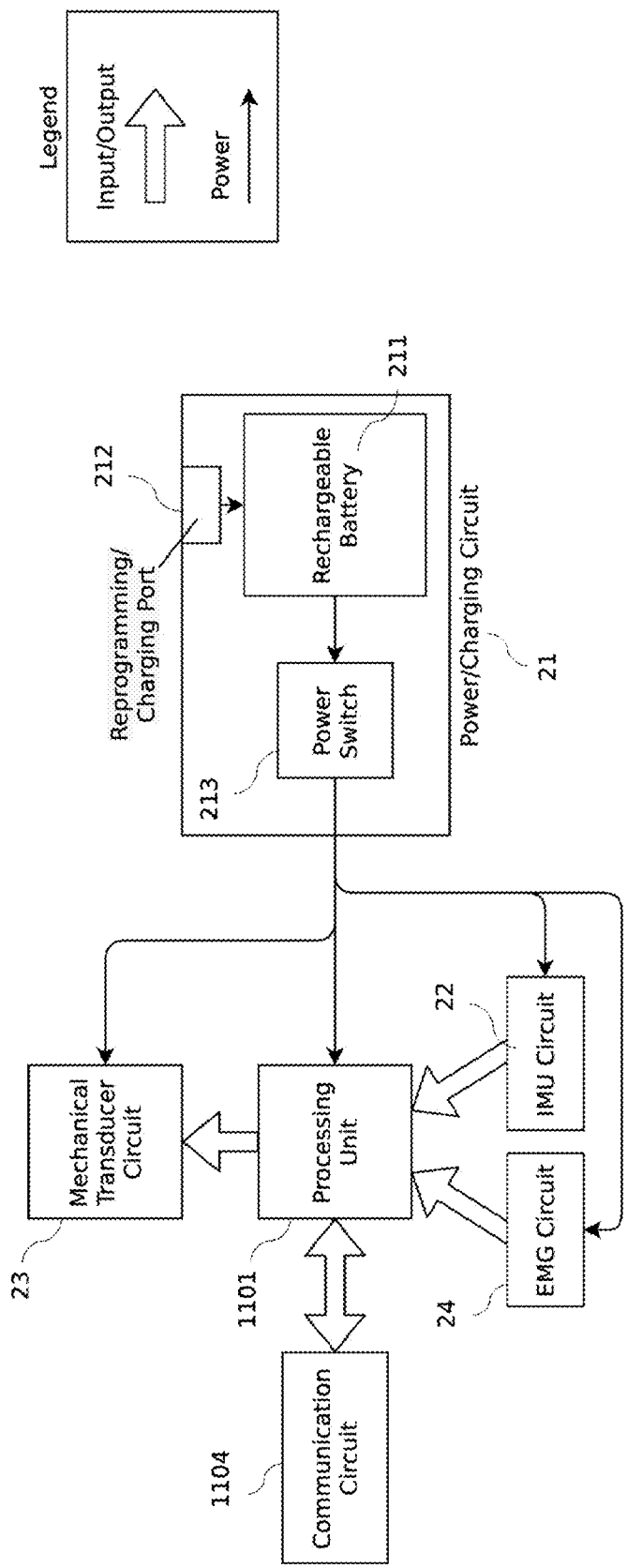
FIG. 2 is an electrical diagram highlighting the main sub-circuits of the system in FIG. 1.

FIG. 2 is an electrical diagram highlighting the main sub-circuits of the system in FIG. 1. FIG. 2 shows the processing unit 1101, which receives body part motional data (e.g. tremor vibration data) from the inertial measurement unit 1108 in the IMU circuit 22. This data is used by the processing unit 1101 to drive the mechanical transducers 1105 in the mechanical transducer circuit 23 at various frequencies and amplitudes. Optionally, the processing unit 1101 may also receive muscle activity data from the electromyography (EMG) sensors 1107 in the EMG circuit 24. The processing unit 1101 can transmit to and receive data from a remote database 16 using a communication module 1104 in the communication circuit 25. The entire system receives power from a rechargeable battery 211 in the power/charging circuit 21. The charging port 212 is used to recharge the battery 211. Optionally, the charging port 212 may also be used to reprogram the processing unit 1101. The power is switched on and off via the power switch 213.

Figure 3:
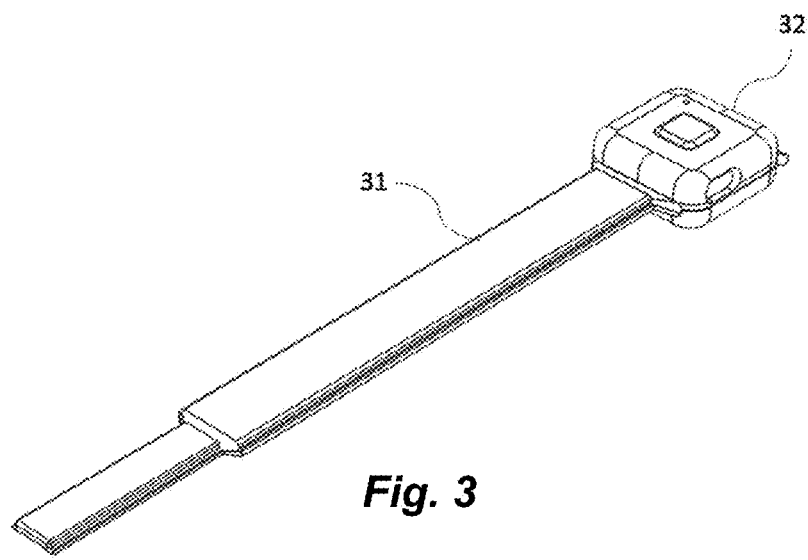
FIG. 3 is an isometric view of a wearable device in accordance with an embodiment of the present invention.

FIG. 3 is an isometric view of a wearable device in accordance with an embodiment of the present invention. FIG. 3 shows the main electronics housing 32 of the device and the band 31 of the device that interfaces with the user's wrist.

Figure 4:
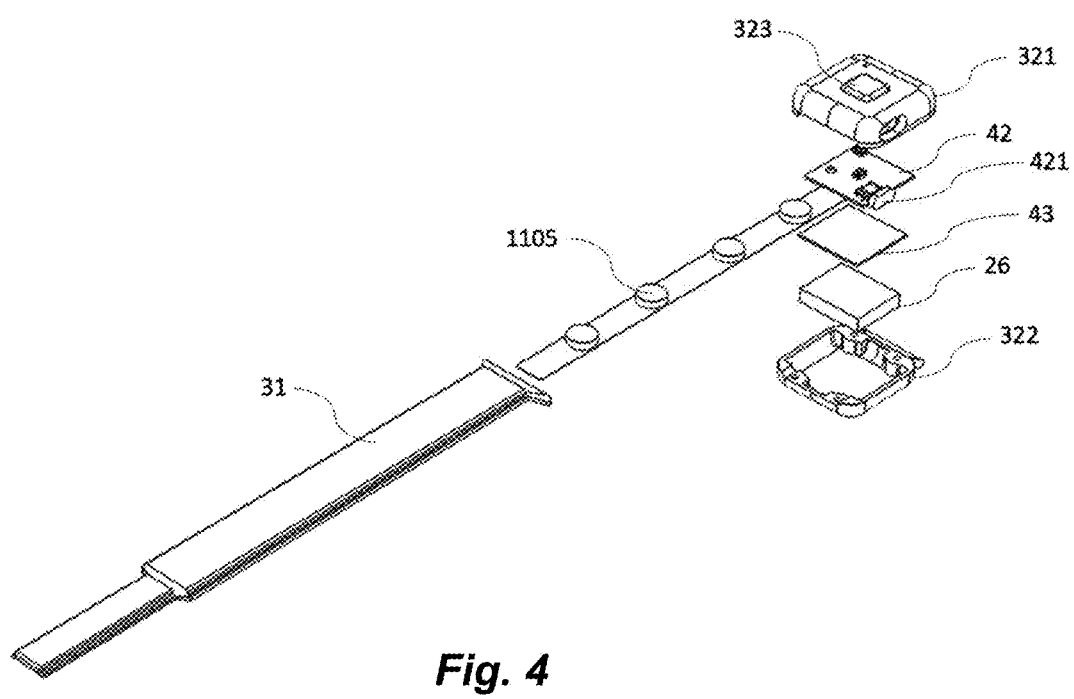
FIG. 4 is an exploded isometric view of a wearable device, in which the vibration motors are housed in the band rather than in the main electronics housing, in accordance with an embodiment of the present invention.

FIG. 4 is an exploded isometric view of a wearable device, in which the vibration motors are housed in the band rather than in the main electronics housing, in accordance with an embodiment of the present invention. The mechanical transducers 1105 are housed in the band 31 which interfaces with the user's wrist. Between the top and bottom halves of the housing 321 322, there is a printed circuit board (PCB) 42, a silicone square to insulate the bottom of the PCB 43, and a rechargeable battery 26. The battery 26 includes protection circuitry to protect from overcharging and unwanted discharging. To recharge the battery 26, a magnetic connector 421, coupled to the battery and mounted in the housing, is inserted into the PCB 42. The magnetic connector 421 couples to a mating connector from an external charger, so that the battery 26 can be conveniently configured for charging by the external charger. The magnetic connector 421 allows patients who have difficulty performing tasks that require fine motor skills to easily charge the device with a magnetic charging cable. The device is intended to work after the patient turns the device on by pressing the single, large button 323 on top of the electronic housing top 321. The button is provided for ease of use by a patient whose fine motor control is affected by a neurological movement disorder.

Figure 5:
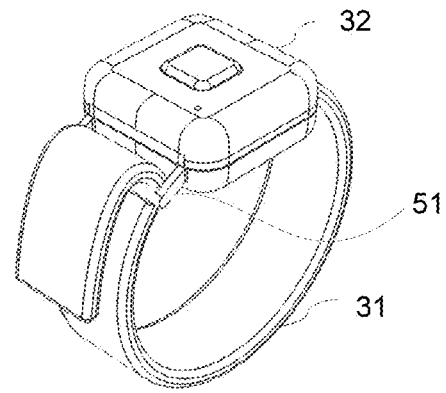
FIG. 5 is an isometric view of a wearable device, in which the device includes a loop mechanism to allow single handed adjustment of the band on the user's wrist, in accordance with an embodiment of the present invention.

FIG. 5 is an isometric view of a wearable device, in which the device includes a loop mechanism 51 to allow single handed adjustment of the band 31 on the user's wrist, in accordance with an embodiment of the present invention. FIG. 5 shows the main electronics housing 32, the band 31 as it looks when worn on the user's wrist, and an adjustment mechanism 51 that is integrated into the main electronics housing 32.

Figure 6:
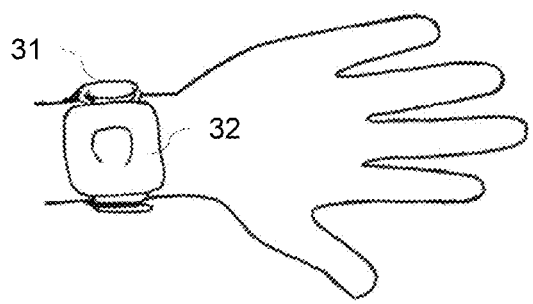
FIG. 6 shows an embodiment of the present invention worn on a hand viewed from above.

FIG. 6 shows an embodiment of the present invention worn on a hand viewed from above. FIG. 6 shows the main electronics housing 32 and the band 31 that interfaces with the user's wrist.

Figure 7:
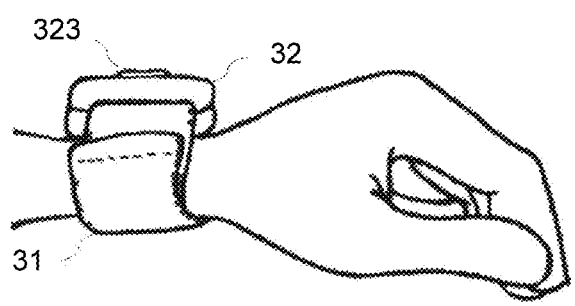
FIG. 7 shows an embodiment of the present invention worn on a hand viewed from the side.

FIG. 7 shows an embodiment of the present invention worn on a hand viewed from the side. FIG. 7 shows the main electronics housing 32, the band 31 that interfaces with the user's wrist, and the on/off button 323 that a patient may use to begin/stop the vibrational stimulation. The on/off button 323 is integrated into the main electronics housing 32.

Figure 8:
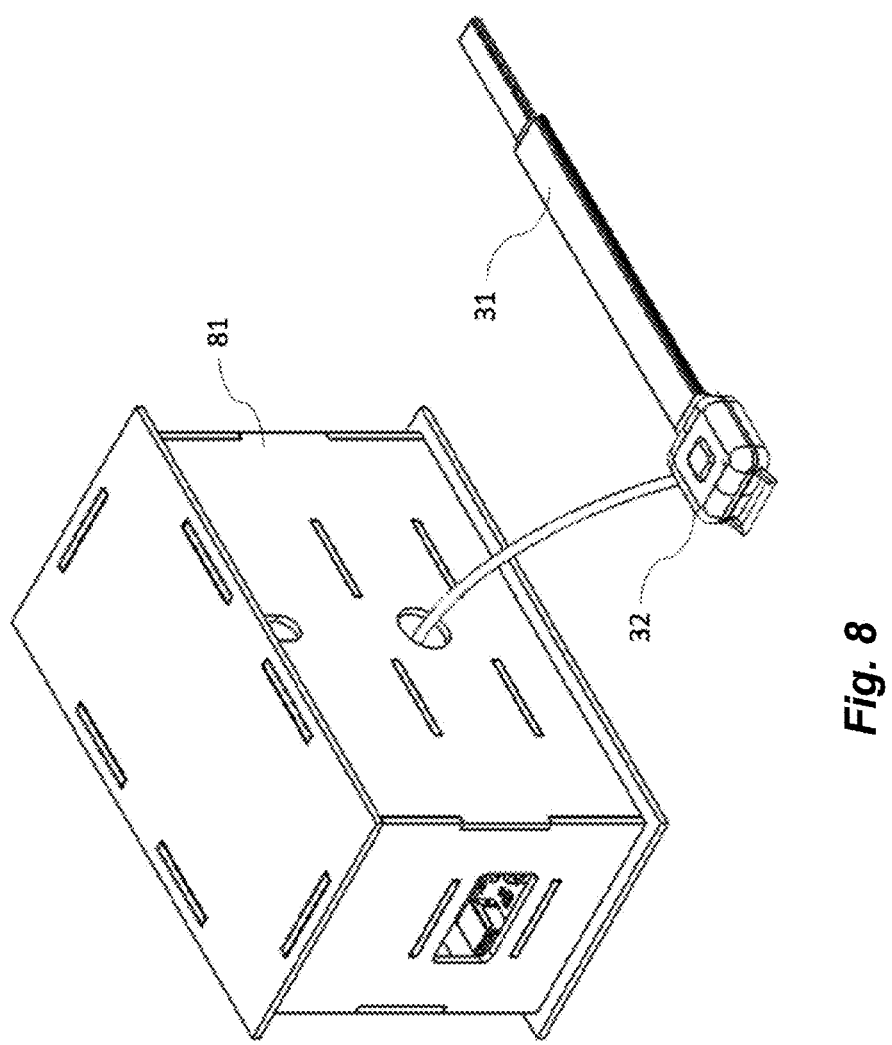
FIG. 8 shows a testing configuration for the wearable medical device, which may be used for more rigorous data collection, in accordance with an embodiment of the present invention.

FIG. 8 shows a testing configuration for the wearable medical device, which may be used for more rigorous data collection, in accordance with an embodiment of the present invention. FIG. 8 shows the main electronics housing 32 and the band 31 that interfaces with the user's wrist. These are connected to a data logging apparatus 81 which collects and stores data. Data can continue to be collected and stored over a larger time scale than on the device alone, as this testing configuration is equipped with a larger processor and storage capacity. At the time of analysis, more complex and computationally heavy data analysis is possible on the collected data stored in the data logging apparatus 81 utilizing the larger processor.

Figure 9:
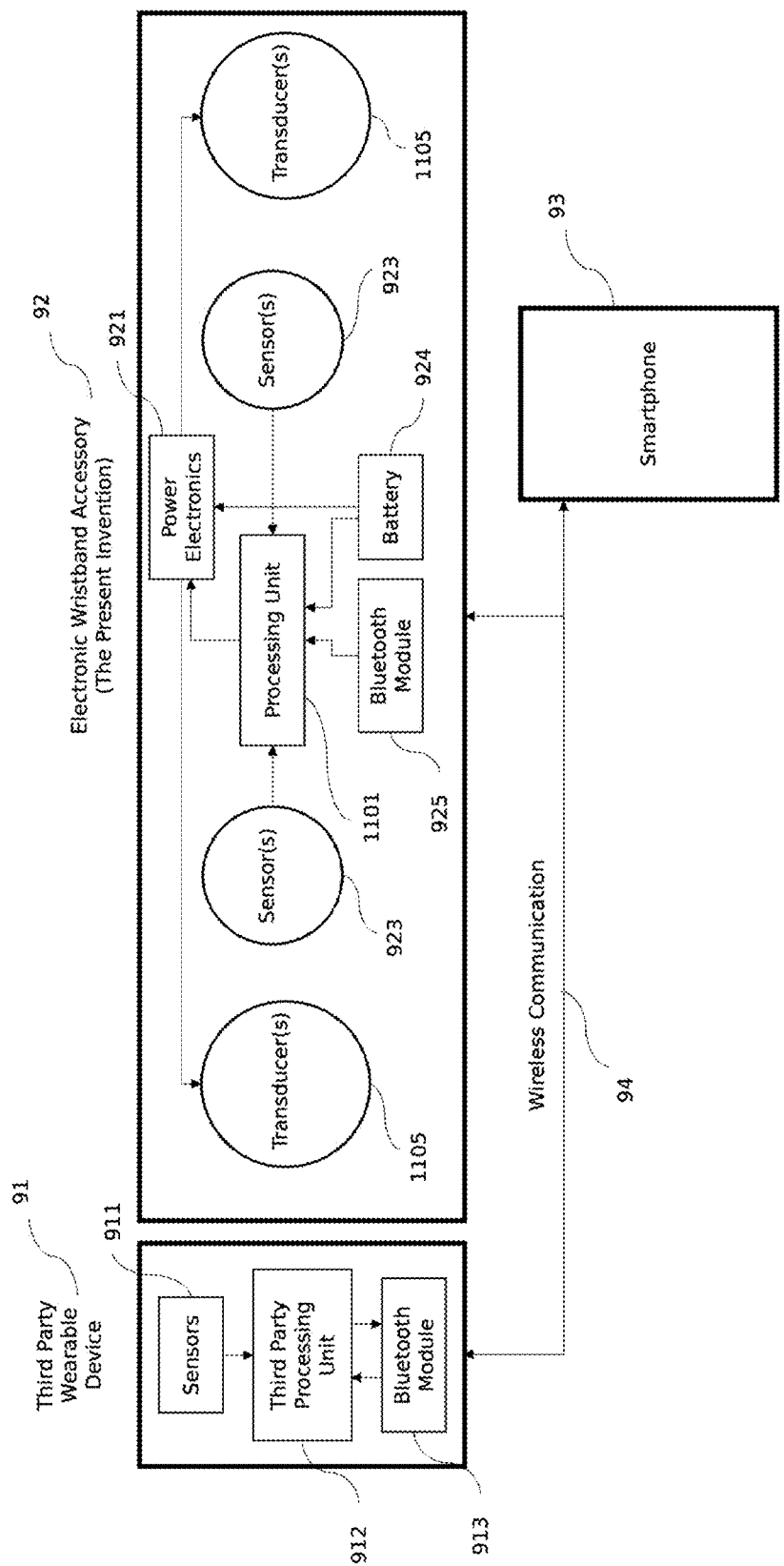
FIG. 9 illustrates a wearable device for mitigating movement disorder, in which the device is an accessory to a third-party smartwatch or other wearable computing device, in accordance with an embodiment of the present invention.

FIG. 9 illustrates a wearable device for mitigating movement disorder, in which the device is an accessory to a third-party smartwatch or other wearable computing device 91, in accordance with an embodiment of the present invention. In such an embodiment, some or all of the computation 912 and sensing 911 are offloaded to the third-party wearable device 91. The third-party device then sends a set of motor commands wirelessly 94 (over Bluetooth for example 913 925) to a processing unit 1101 on the accessory band 92. This processing unit 1101 interfaces with the transducers 1105 on the band to execute the desired motor commands. In this embodiment, the accessory band 92 has its own battery 924. In some embodiments, the band also has its own specialized sensors 923 (such as electromyography sensors), the signals of which are communicated to the third-party processing unit 912 via the accessory processing unit 1101, and wireless communication 913 925 94. Data may also be logged to the user's smartphone 93 over the same wireless connection 94.

Figure 10:
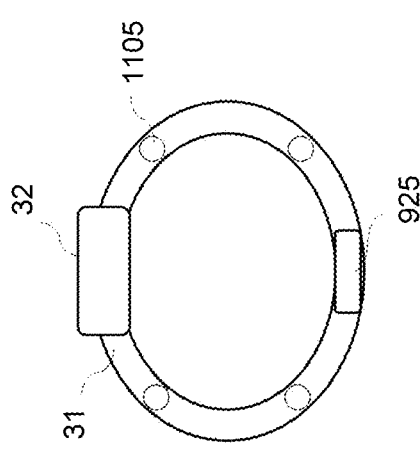
FIG. 10 shows a side view of a wearable device, which is as an accessory band for a third-party smartwatch or other wearable computing device, in accordance with an embodiment of the present invention.

FIG. 10 shows a side view of a wearable device, which is as an accessory band for a third-party smartwatch or other wearable computing device, in accordance with an embodiment of the present invention. It shows the main electronics housing 32 and the band 31 which contains the mechanical transducers 1105. The band 31 interfaces with the user's wrist. This view illustrates an example placement of the accessory battery 925 and processing unit 1101.

Figure 11:
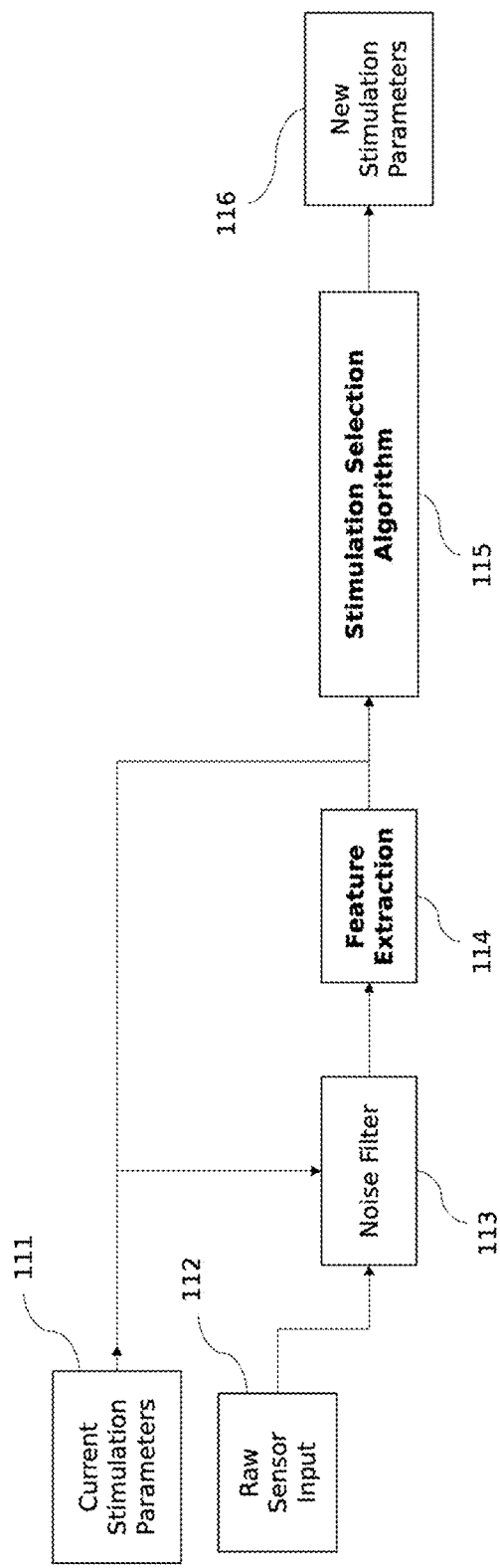
FIG. 11 shows a process by which a raw sensor input is used to compute a set of stimulation parameters, in accordance with an embodiment of the present invention.

FIG. 11 shows a process by which a raw sensor input may be used to compute a set of stimulation parameters in accordance with an embodiment of the present invention. The stimulation parameters are continuously updated in closed loop. These parameters can include any quantities used to define a stimulation waveform such as frequency, amplitude, phase, duty cycle, etc. At each iteration of the update loop, the current stimulation parameters 111 and raw sensor input 112 are used to filter out transducer/sensor crosstalk 113 either by using knowledge of the output waveform to subtract from the sensed waveform or by using knowledge of the timing of the output waveform to limit sensing to the "off" phases of a pulsing stimulation. This filtering subsequently allows for feature extraction 114 of the raw sensor input 112. The stimulation selection algorithm 115 then uses the current stimulation parameters 111 and the extracted features 114 to select new stimulation parameters 116. This process is illustrated in greater depth in FIG. 13. When the process repeats, the previously new stimulation parameters 116 become the current stimulation parameters 111.

Figure 12:
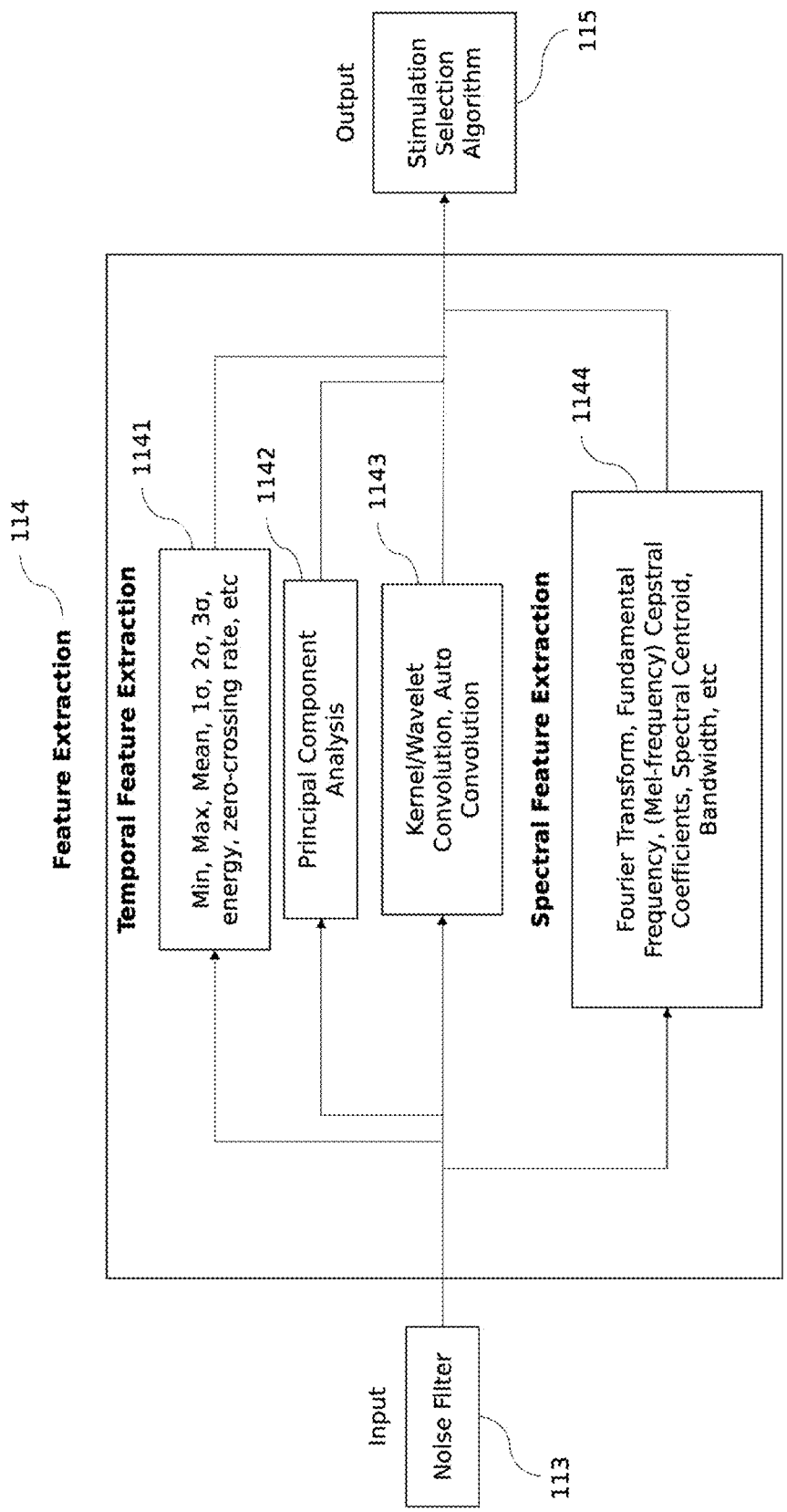
FIG. 12 shows a feature extraction process, in accordance with an embodiment of the present invention.

FIG. 12 shows a feature extraction process 114 in accordance with an embodiment of the present invention. This process takes in a filtered sensor signal 113, as described with respect to FIG. 11, and extracts temporal features 1141 1142 1143 and/or spectral features 1144. Examples of common temporal features include the minimum value, the maximum value, first three standard deviation values, signal energy, root mean squared (RMS) amplitude, zero crossing rate, principal component analysis (PCA), kernel or wavelet convolution, or autoconvolution. Examples of common spectral features include the Fourier Transform, fundamental frequency, (Mel-frequency) Cepstral coefficients, the spectral centroid, and bandwidth. Features are extracted with standard digital signal processing techniques onboard the main processing unit of the device. The set of collected features is then fed into the stimulation selection algorithm 115.

Figure 13:
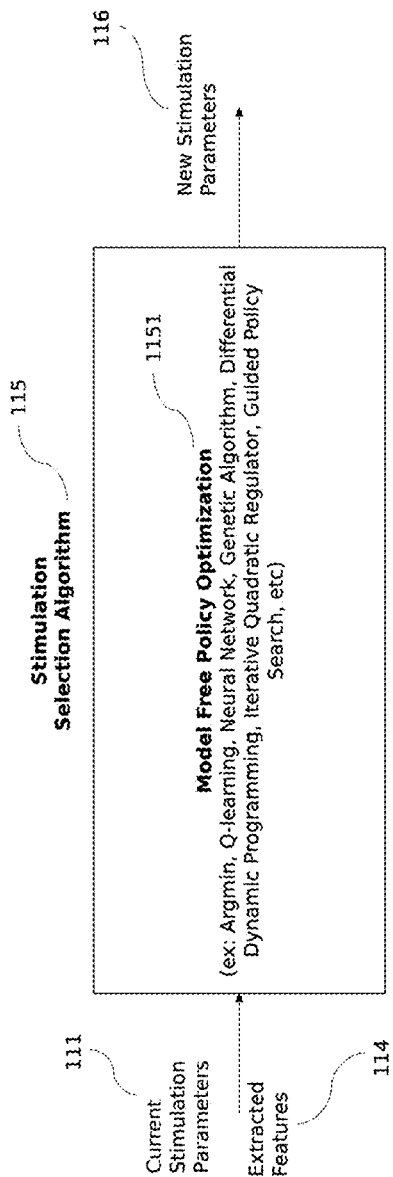
FIG. 13 shows a stimulation optimization algorithm, in accordance with an embodiment the present invention.

FIG. 13 shows a stimulation optimization algorithm 115 in accordance with an embodiment the present invention. The stimulation selection algorithm takes in the extracted features 114 and the current stimulation parameters 111 and uses them to determine the set of new stimulation parameters 116. The process by which the new parameters are determined is an optimization 1151 to minimize the symptom severity. Given that there is no analytical model for the symptom's response to stimulation patterns, this optimization is inherently model free. Examples of model free policy optimization techniques are argmin (or minimization over the set of input arguments), Q-learning, neural networks, genetic algorithms, differential dynamic programming, iterative quadratic regulator, and guided policy search. Descriptions of some such algorithms can be found in Deisenroth, M. P. (2011), "A Survey on Policy Search for Robotics," *Foundations and Trends in Robotics*, 2 (1-2), 1-142. doi: 10.1561/2300000021; and Beasley, D., Bull, D. R., & Martin, R. (1993), "An Overview of Genetic Algorithms: Part 1, Fundamentals," 1-8, (herein incorporated, in their entirety, by reference).

In an example, an extracted feature may be the amplitude of the tremor and the set of current stimulation parameters can be a stimulation waveform. A stimulation selection algorithm can then compare the tremor amplitude observed with the current set of stimulation parameters to the tremor amplitude observed with a previous set of stimulation parameters to determine which of the two sets of stimulation parameters resulted in the lowest tremor amplitude. The set with the lowest resulting tremor amplitude could then be used as the baseline for the next iteration of the stimulation selection algorithm which would compare it to a new set.

Two example stimulation selection algorithms that may be used in embodiments follow:

---

Algorithm 1 Determine Optimal Vibration Motor State

---

Input: Feed of x, y, z accelerometer data
Output: Output state which minimizes tremor magnitude
1:     AmplitudeStates = $\{A_1, A_2, \ldots, A_n\} = \{A\}_n$
2:     FrequencyStates = $\{F_1, F_2, \ldots, F_m\} = \{F\}_m$
3:     OutputStates = $\{A \times F\}_{n \times m}$
4:     TremorResponses = $\{0\}_{n \times m}$
5:
6:     for State in OutputStates do
7:         Output ← State
8:         TremorResponses[State] ← ReadAccelerometer
9:     $OptimalState \leftarrow \underset{\{A\},\{F\}}{\operatorname{argmin}} TremarResponses$

---

Algorithm 2 Q-learning Algorithm

---

Input: Feed of x, y, z accelerometer data
Output: Output state which minimizes tremor magnitude
1:     AmplitudeStates = $\{A_1, A_2, \ldots, A_n\} = \{A\}_n$
2:     FrequencyStates = $\{F_1, F_2, \ldots, F_m\} = \{F\}_m$
3:     OutputStates = $\{A \times F\}_{n \times m} = S$
4:     Choices = {IncreaseAmplitude, IncreaseFrequency} = C
5:     QTable = Q:S × C → R
6:     for Epoch in MaxEpochs do
7:         for s in OutputStates do
8:             for c in Choices do
9:                 r ← ReadAccelerometer
10:   $Q(s, c) \leftarrow (1 - \alpha) \cdot Q(s, c) + \alpha \cdot \left( r + \gamma \cdot \min_{k \in C} Q(s + l, k) \right)$
11:     $OptimalState \leftarrow \underset{s}{\operatorname{argmin}} Q$

---

In some embodiments, the structure of the output stimulation pattern may be a weighted average of optimized patterns corresponding to each symptom, where the weights are proportional to the symptom severity relative to the other observed symptoms. In some embodiments, the structure of the output stimulation pattern may just be the pattern optimized to reduce the most severe symptom.

Figure 14:
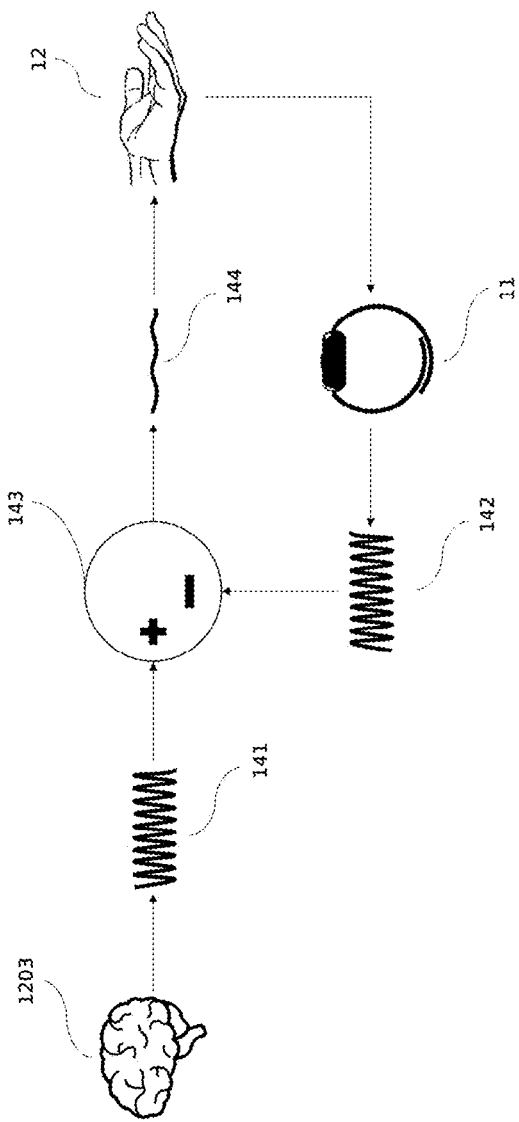
FIG. 14 shows a neurological signal cancelling system, illustrating how the wearable device and body interact, in accordance with an embodiment of the present invention.

FIG. 14 shows a neurological signal cancelling system, illustrating how the wearable 11 device and body 12 interact, in accordance with an embodiment of the present invention in which the body and the device are considered collectively as an operative system. The system includes the user's nervous system 1203, which sends control signals 141 to the body 12. As a further aspect of the system, the wearable 11 senses the body's movement and sends an opposing control signal 142 which is defined by the output of the active noise cancellation algorithm 143. The control signals 141, 142 undergo a signal cancelling process within the nervous system of the user 1203, which results in a smoother perceived motion signal 144.

Figure 15:
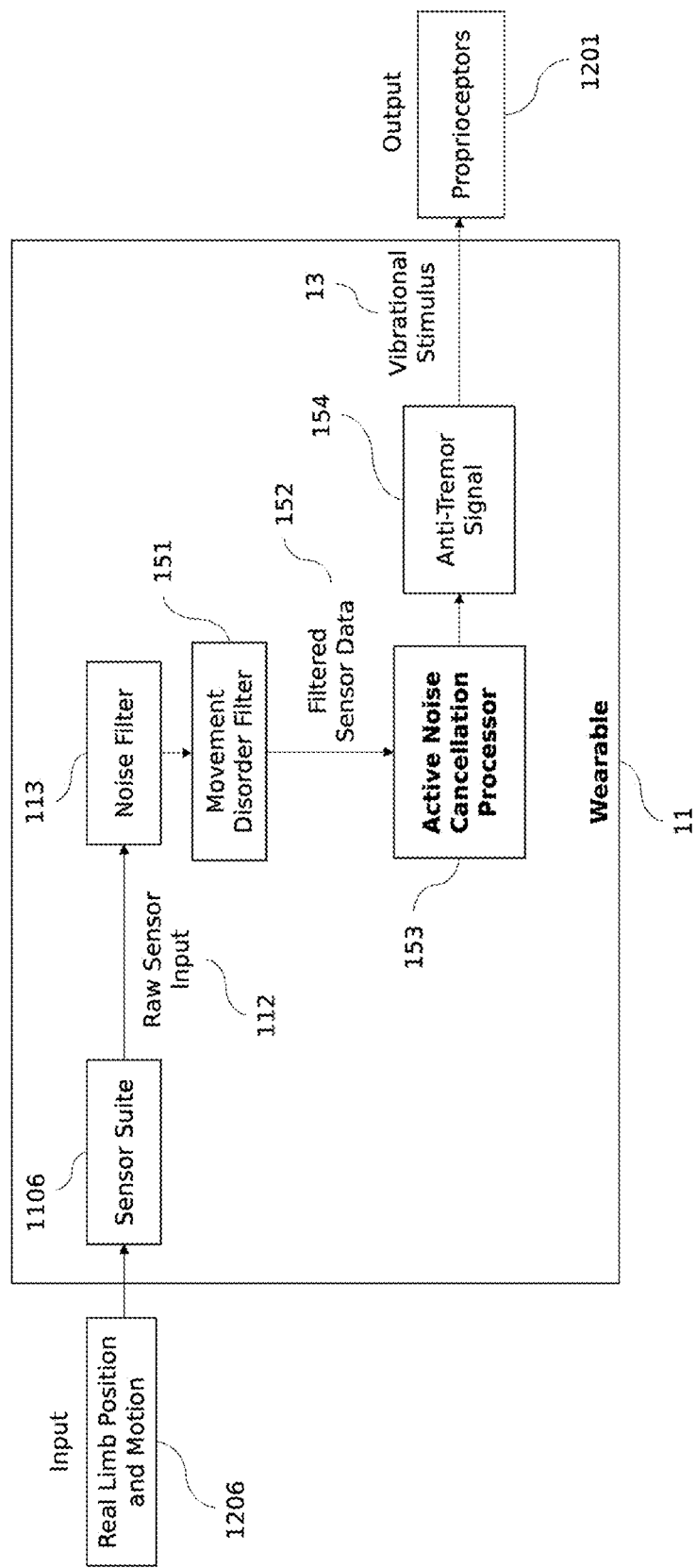
FIG. 15 shows a process in which the raw sensor input may be processed using active noise cancellation to compute a set of stimulation parameters, in accordance with an embodiment of the present invention.

FIG. 15 shows a process in which the raw sensor input 112 may be processed using active noise cancellation to compute a set of stimulation parameters, in accordance with an embodiment of the present invention. In FIG. 15, the suite of movement disorder sensors 1106 within the device 11 quantify the real limb position and motion 1206 to produce a raw sensor input 112, which is then filtered using both a noise filter 113 and a movement disorder filter 151. The noise filter 113 may use either knowledge of the output waveform to subtract from the sensed waveform or knowledge of the timing of the output waveform to limit sensing to the "off" phases of a pulsing stimulation. The movement disorder filter 151 uses a 0-15 Hz bandpass filter to eliminate any other signal components not caused by a movement disorder. The resultant filtered sensor data 152 is then fed to the active noise cancellation processor 153, which generates the anti-tremor stimulation signal 154. The active noise cancellation processor 153 is described in further detail in connection with FIGS. 16 and 17. The device 11 uses vibrational stimulus 13 to transmit the anti-tremor stimulation signal 154 to the proprioceptors 1201 of the user's body. Information on the body's reaction to the anti-tremor stimulation signal can be found in further detail in connection with FIG. 1.

Figure 16:
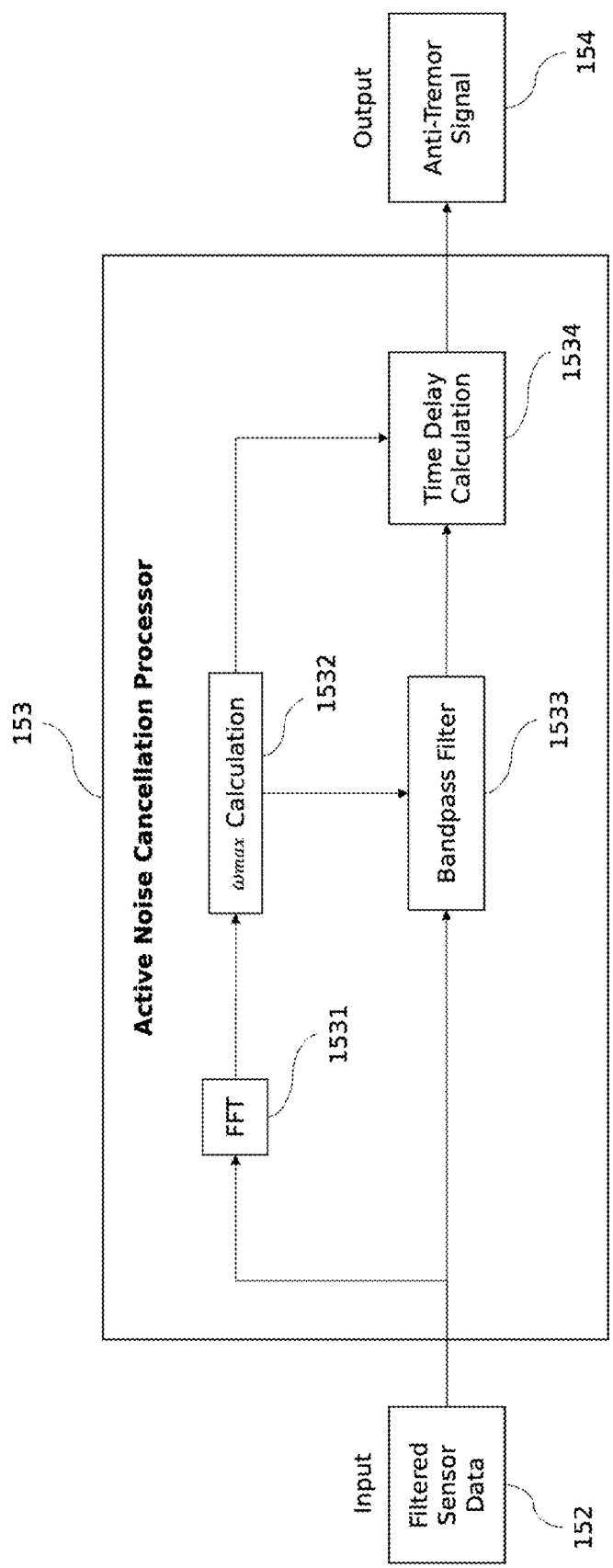
FIG. 16 shows one exemplary embodiment of the process of anti-tremor stimulation signal generation by the active noise cancellation (ANC) processor.

FIG. 16 shows one exemplary embodiment of the process of anti-tremor stimulation signal 154 generation by the active noise cancellation (ANC) processor 153. The ANC processor 153 takes the resulting filtered sensor data 152 of FIG. 15 as input, which is then transformed into the frequency domain by applying a Fourier Transform 1531. By definition, the fundamental frequency, @max, the frequency having the greatest amplitude, is selected through argmax 1532 of the frequency domain data from the Fourier Transform 1531, and the output is used as the center of a bandpass filter 1533 to ensure an accurate time delay calculation 1534. For example, if the fundamental frequency is calculated to be 10 Hz, then one exemplary embodiment of the bandpass filter 1533 may be set at 8-12 Hz. The fundamental frequency is also used to calculate the time delay 1534 necessary to achieve a phase offset, in degrees, such that the resulting signal behaves as negative feedback. Time delay to achieve a phase offset of x is equal to $$\frac{x}{360*\text{frequency}}.$$

This filtered and delayed signal is output as the anti-tremor stimulation signal 154. This process can be repeated for the 2nd through $N^{th}$ fundamental frequencies.

Figure 17:
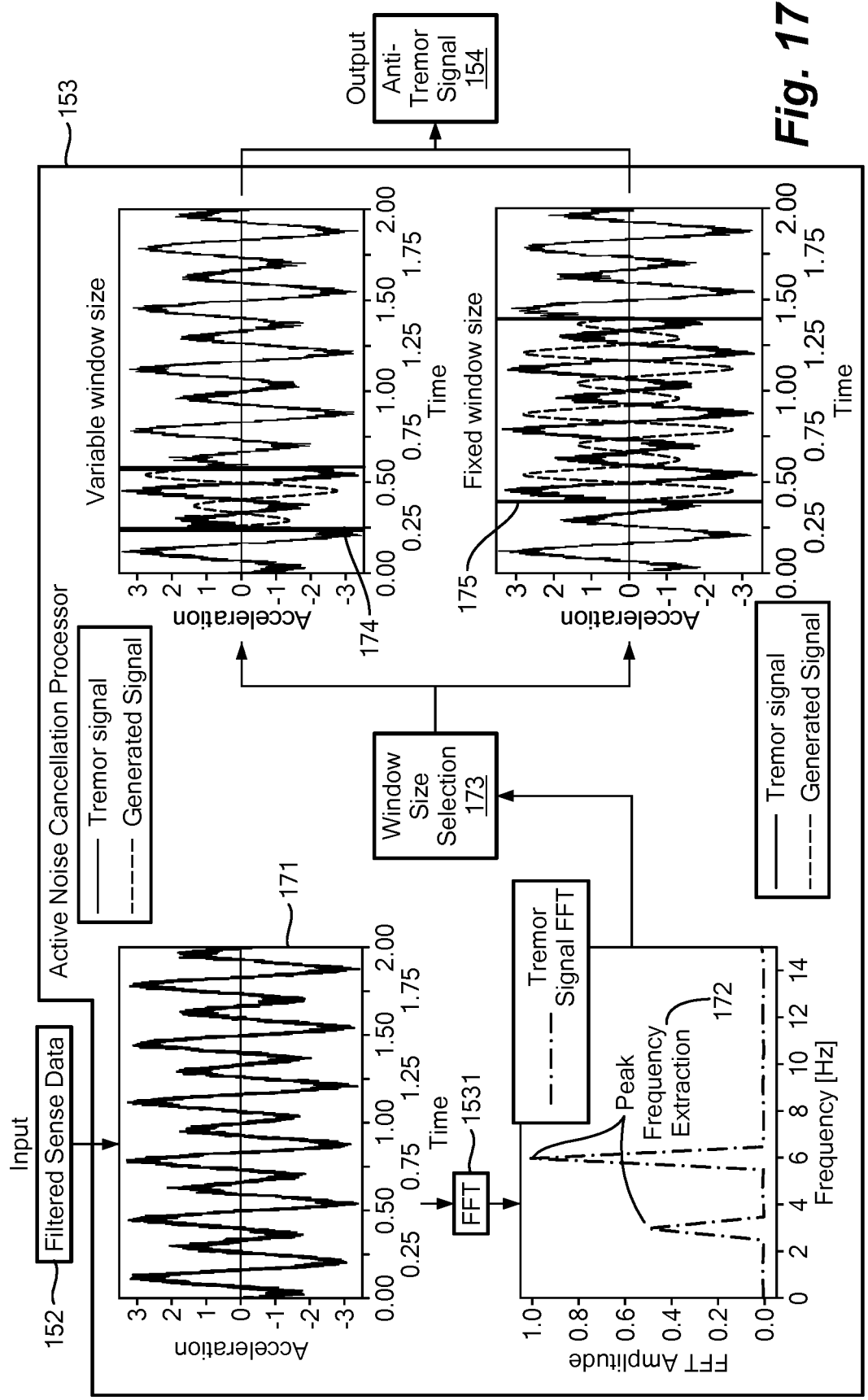
FIG. 17 shows another exemplary embodiment of the process of anti-tremor stimulation signal generation by the ANC processor.

FIG. 17 shows another exemplary embodiment of the process of anti-tremor stimulation signal 154 generation by the ANC processor 153. The ANC processor 153 takes filtered sensor data 152 from an inertial motion unit (IMU) and calculates the resultant limb acceleration 171. The limb acceleration 171, in the time domain, is then transformed into the frequency domain by applying a Fourier Transform 1531, allowing the ANC processor 153 to extract the peak frequencies 172 of the limb acceleration using general peak finding algorithms, which take a set of data and return a set of local maxima, or peaks, such that the data points on either side of the peaks are less than said maxima. The ANC processor 153 selects the window size 173 of the acceleration 171 by use of one of two methods.

The first method 174 uses the lowest peak frequency to calculate the window size. Selecting the lowest peak frequency ensures that all the relevant features of the limb acceleration 171 are captured in the window and able to be properly reproduced when generating the anti-tremor stimulation signal 154. This method involves inverting the lowest peak frequency, which corresponds to the lowest frequency feature in the limb acceleration 171, and converting it into the time domain [Hz=1/s]. In FIG. 17, the lowest peak frequency is 3 Hz, so the window size is ⅓ s.

The second method 175 uses a window size of fixed length. The acceleration data captured in the selected fixed window size is then inverted and becomes the anti-tremor stimulation signal 154 output. The lower bound of acceptable window size is found using the first method 174, the time domain conversion of the lowest peak frequency. A window smaller than this would fail to capture all of the relevant features of the limb acceleration 171. Theoretically, there is no upper bound of acceptable window size 173, but in practice, the upper bound will depend on the available memory of the device 11.

Figure 18:
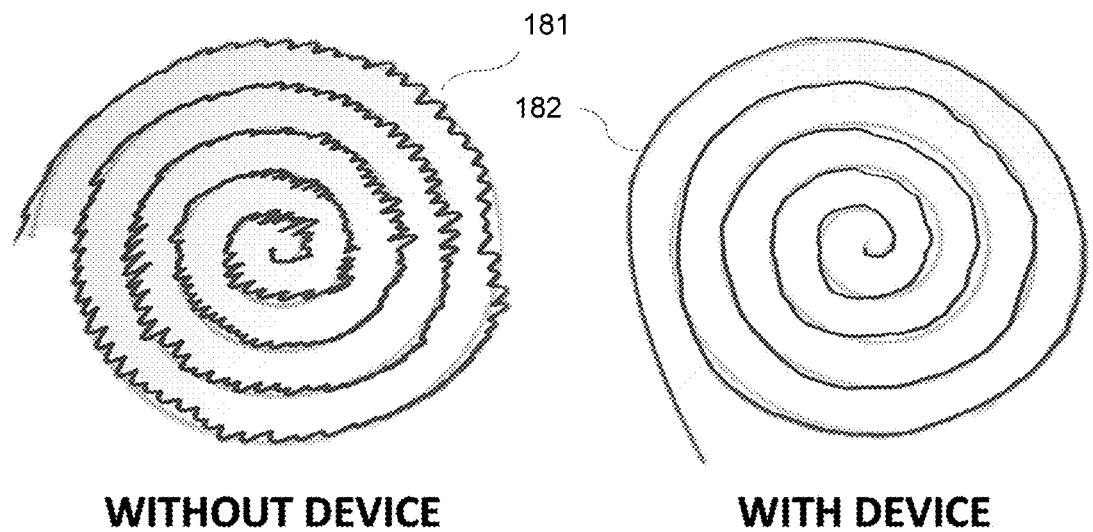
FIG. 18 is a pair of renderings by a Parkinson's patient of a spiral under conditions without and with treatment by a device in accordance with an embodiment of the present invention.

FIG. 18 is a pair of renderings 181 and 182 by a tremor patient of an Archimedes spiral under conditions without and with treatment by a device in accordance with an embodiment of the present invention. The spiral tracing test allows doctors to gain insight on the frequency, amplitude, and direction of their patients' tremors. It can also inform the doctor of abnormal movement of hypokinesia, dystonia, and tremor. The task requires the patient to continuously trace the Archimedes spiral. Patients who have tremors will have difficulty following the spiral and will trace off the spiral line resulting in a disordered spiral 181. Wearing a device in accordance with an embodiment of the present invention, the patient is able to trace the spiral more accurately resulting in a smoother spiral 182.

Figure 19:
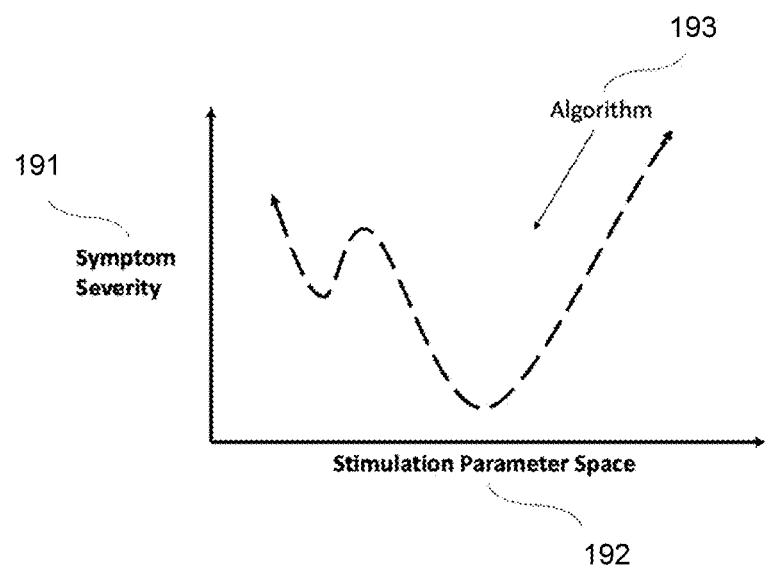
FIG. 19 illustrates an embodiment of a simple non-convex gradient descent optimization used in embodiment of the present invention for symptom reduction by searching over the parameter configuration space.

FIG. 19 illustrates an embodiment of a simple non-convex gradient descent optimization used in an embodiment of the present invention for symptom reduction by searching over the parameter configuration space. It is a graphical representation of the stimulation selection algorithm 193 associated with the present invention. The algorithm 193 moves through the stimulation parameter space 192 and attempts to minimize symptom severity 191. The movement through the stimulation parameter space involves trying different sets of stimulation parameters and comparing their resulting symptom severities as quantified by their respective sensors. The algorithm attempts to minimize symptom severity by testing different sets of parameters until an optimal set for minimizing symptom severity is found.

Diagnostic Applications. Alternative benchtop versions of the device can be used to elicit tremors in Parkinson's patients for the purposes of early detection. This is done using the same mechanisms as in reducing tremor but using an inverted stimulation parameter search heuristic. User testing has shown that for each patient, there exists a stimulation pattern which when applied to the Parkinson's patient with very slight tremor will produce a very large tremor. This effect does not occur in users who do not have Parkinson's Disease. This phenomenon can be used for earlier detection and diagnosis of Parkinson's Disease which can be difficult to diagnose. For instance, provided herein is a method of diagnosing a movement disorder in a body part of a susceptible subject comprising: using a processor, providing a stimulation signal to a transducer in order to induce symptoms of a movement disorder; applying, through the transducer, the stimulation signal to a user; receiving movement data, related to movement of the user, from a sensor; filtering the movement data to remove noise to produce a filtered signal; processing the filtered signal to (a) transform the movement data into frequency data, (b) use the frequency data to determine a fundamental frequency of the movement of the user, and processing the frequency data to determine if the user is suffering from the movement disorder.

Figure 20:
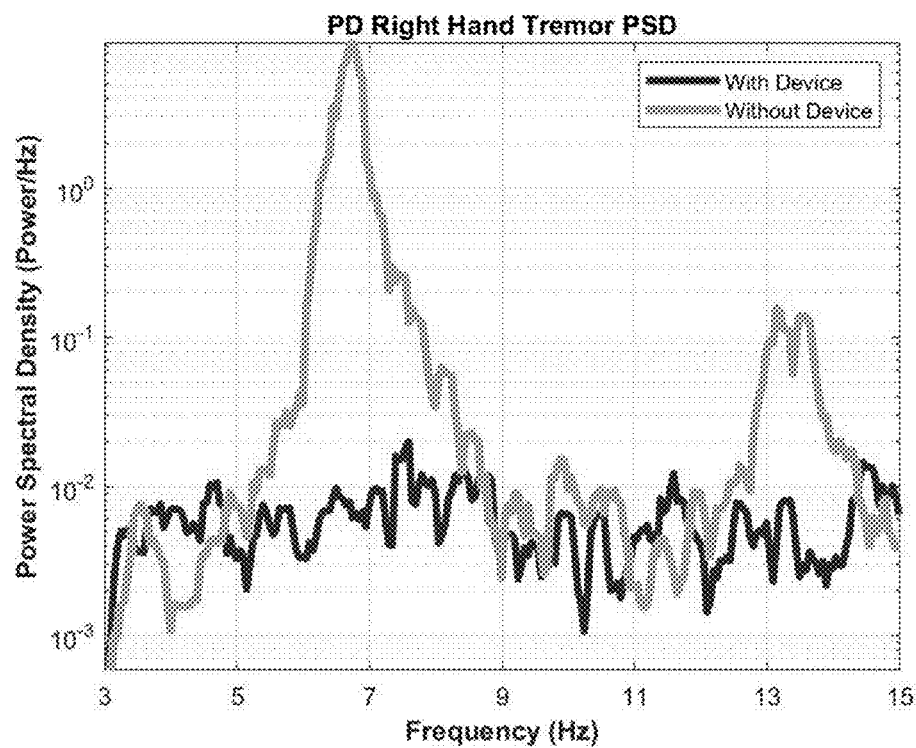
FIG. 20 shows a power spectral density (PSD) plot of the postural tremor of a Parkinson's Disease patient with and without the use of a device in accordance with an embodiment of the present invention.
Figure 21:
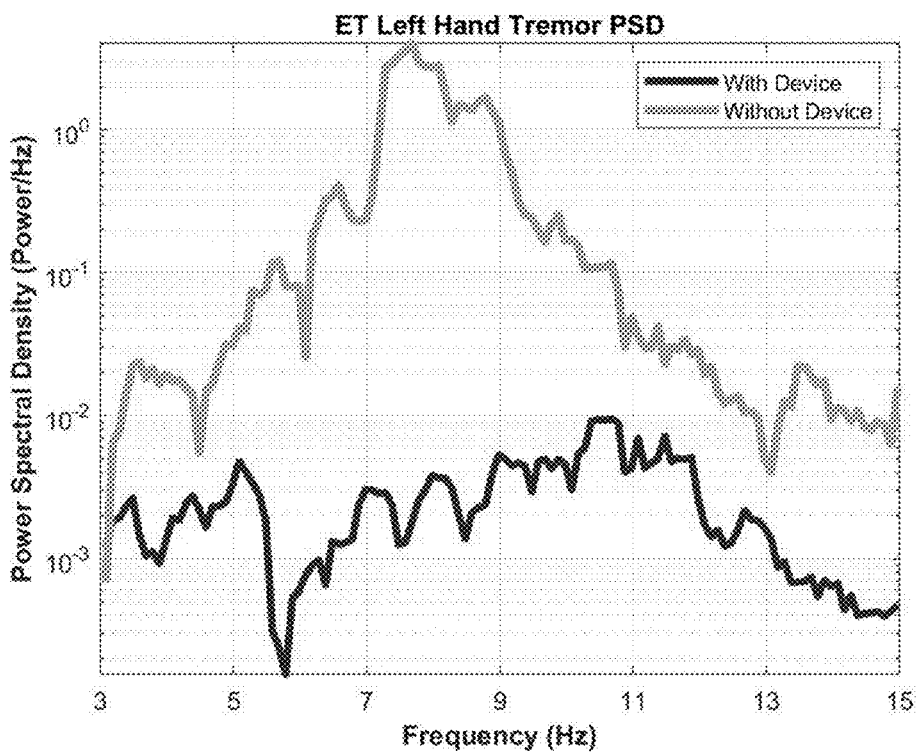
FIG. 21 shows a power spectral density (PSD) plot of the postural tremor of an Essential Tremor patient with and without the use of a device in accordance with an embodiment of the present invention.

Patient Studies. FIGS. 20 and 21 each show a power spectral density (PSD) plot of the postural tremor of a Parkinson's Disease and Essential Tremor patient, respectively, with and without the use of a device in accordance with an embodiment of the present invention. The data was taken by asking each patient to hold his or her hand out for 10 seconds, with and without the device. In FIGS. 20 and 21, tremor amplitude is compared with and without the device.

The following describes a test case of an embodiment of the present invention. Participants were asked to trace a printed Archimedes Spiral, a common test used to diagnose Parkinson's, with and without the device, as shown in FIG. 18. The results were measured by using image processing software to evaluate the accuracy of the traced spirals. In the first round of testing, the device was tested on around 20 participants with Parkinson's and 1 participant with a resting tremor. The majority of the participants, however, either did not experience tremors or were already being treated for Parkinson's and only experienced slight tremors. It was observed that the reduction in tremor severity was strongly correlated to the initial tremor severity. That is, patients with minimal tremors experienced minimal benefit while patients with more extreme tremors experienced more dramatic benefit. The participant with the most severe postural tremor, caused by Parkinson's Disease, saw the most improvement in performance as shown in FIG. 20. Another participant with a postural tremor, caused by Essential Tremor, also showed significant improvement as shown in FIG. 21. The results were repeatable with both of these participants. Participants who suffered from rigidity observed that they had a larger range of movement in their hands and completed their spiral tests faster with the device than without.

Figure 22:
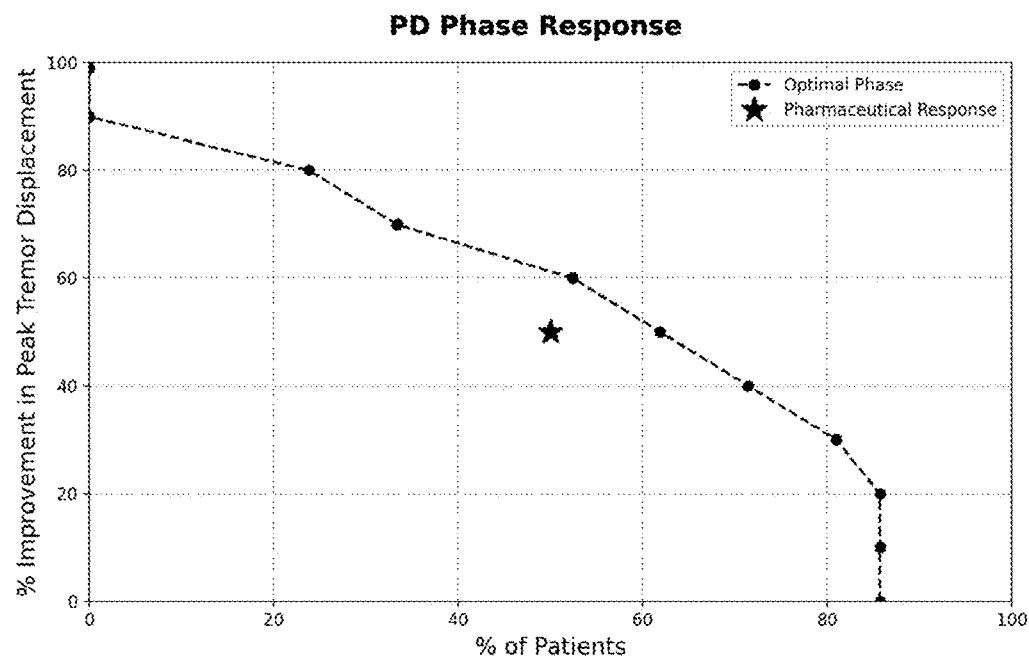
FIG. 22 shows the tremor response of 21 PD patients in peak tremor displacement when stimulation was applied using the process of anti-tremor stimulation signal generation by varying the phase rotation of the stimulation, and selecting the phase rotation which results in the greatest tremor mitigation.
Figure 23:
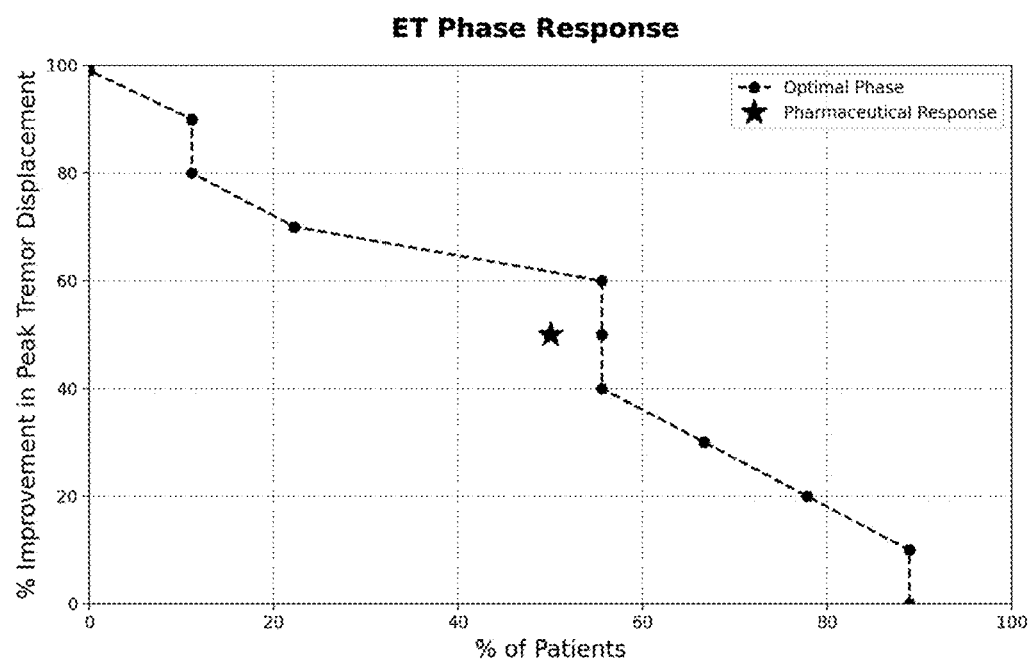
FIG. 23 shows the tremor response of 8 ET patients in peak tremor displacement when stimulation was applied using the process of anti-tremor stimulation signal generation by varying the phase rotation of the stimulation, and selecting the phase rotation which results in the greatest tremor mitigation.

FIGS. 22 and 23 show the tremor response of 21 PD and 8 ET patients, respectively, in peak tremor displacement when stimulation was applied using the process of anti-tremor stimulation signal generation by varying the phase rotation of the stimulation, and selecting the phase rotation which results in the greatest tremor mitigation. Using this method, the frequency of the stimulation was chosen by the active noise cancellation (ANC) processor, and thus varied between patients, but each patient's testing session was performed at a singular frequency.

Figure 24:
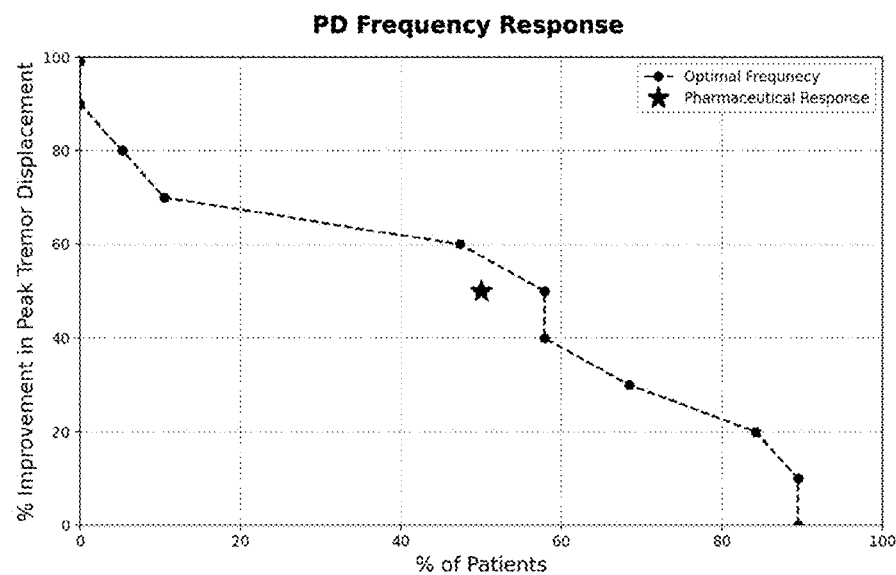
FIG. 24 shows the tremor response of 19 PD patients in peak tremor displacement when stimulation was applied using the process of anti-tremor stimulation signal generation by varying the frequency of the stimulation, and selecting the frequency which results in the greatest tremor mitigation.
Figure 25:
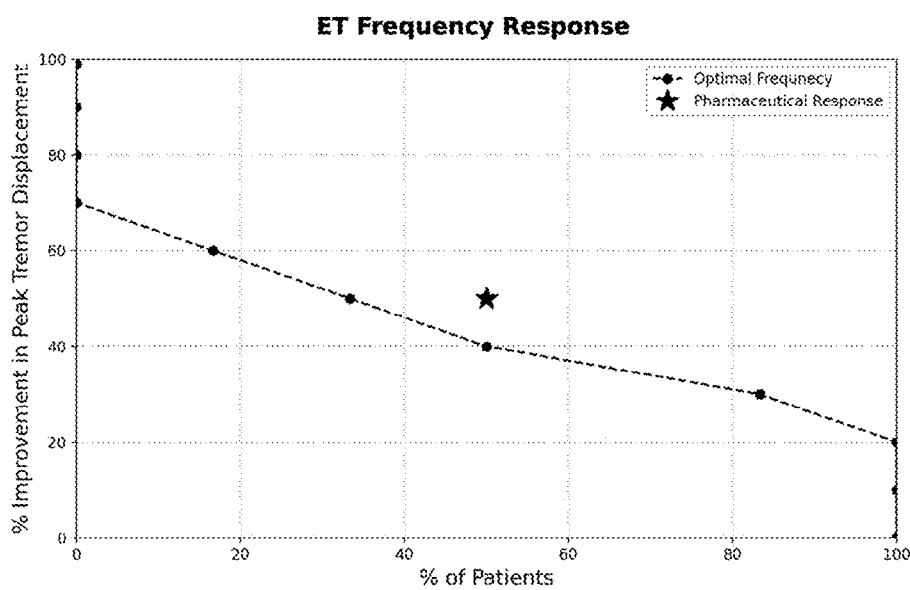
FIG. 25 shows the tremor response of 6 ET patients in peak tremor displacement when stimulation was applied using the process of anti-tremor stimulation signal generation by varying the frequency of the stimulation, and selecting the frequency which results in the greatest tremor mitigation.

FIGS. 24 and 25 show the tremor response of 19 PD and 6 ET patients, respectively, in peak tremor displacement when stimulation was applied using the process of anti-tremor stimulation signal generation by varying the frequency of the stimulation, and selecting the frequency which results in the greatest tremor mitigation. The phase rotation was not modulated.

The following describes a test case of an embodiment of the present invention. Participants were asked to perform a number of tasks in which their tremor was observed both with and without stimulation. The tasks were extracted from validated scales for upper limb tremor evaluation in both PD and ET, the MDS-UPDRS (Movement Disorder Society-Unified Parkinson's Disease Rating Scale) and TETRAS (The Essential Tremor Rating Assessment Scale), respectively. To evaluate postural tremor, participants were asked to hold their arm out in front of their body. To evaluate kinetic tremor, participants were asked to start with their arm outstretched, then move their finger back to touch their nose, and back to the outstretched position. To evaluate resting tremor, participants were asked to relax with their arms resting on a surface, with their eyes closed and counting backwards from 100. During each task, the participant will perform the movement for 80 seconds, with the vibratory stimulation switching off and on every 20 seconds. During treatment stimulation, the participant will randomly start with either option A (treatment) or option B (no treatment) for 10 seconds, followed by a rest period for 10 seconds to account for potential carryover effects. After the break, a crossover occurs and the participant who received option A will receive option B and vice versa for 10 seconds. Participants then take another 10 second break before repeating the randomization and crossover once more. The results in FIGS. 22-25 show the best response for each participant.

Included Embodiments. While the above embodiments reference accelerometers, vibration motors, microUSB, and wristbands the invention is not limited to such implementations. Additionally, the above embodiments are not intended to limit the scope of the invention. For example, various modifications and variations of interfaces, types of electromyography sensors, gyroscopes, inertial measurement units, piezoelectrics, electromagnets, electropermanent magnets, pneumatics, voice coils, hydraulics, resistive heating elements should be included. The scope of form factors should also include headbands, collars, anklets, armbands, and rings. The scope of electrical interfaces should include Thunderbolt cables, USB, USB C, microUSB, wireless communication, wireless charging, and Bluetooth communication.

The present invention may be embodied in many different forms, including, but in no way limited to, computer program logic for use with a processor (e.g., a microprocessor, microcontroller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof.

Computer program logic implementing all or part of the functionality previously described herein may be embodied in various forms, including, but in no way limited to, a source code form, a computer executable form, and various intermediate forms (e.g., forms generated by an assembler, compiler, networker, or locator.) Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink wrapped software or a magnetic tape), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

While the invention has been particularly shown and described with reference to specific embodiments, it will be understood by those skilled in the art that various changes in form and detail may be made therein without departing from the spirit and scope of the invention as defined by the appended clauses. While some of these embodiments have been described in the claims by process steps, an apparatus comprising a computer with associated display capable of executing the process steps in the claims below is also included in the present invention. Likewise, a computer program product including computer executable instructions for executing the process steps in the claims below and stored on a computer readable medium is included within the present invention.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A wearable device for modulating movement disorder symptoms of a user, the device comprising:
   a. a housing;
   b. an attachment system coupled to the housing and configured to attach to a user;
   c. a sensor disposed in the housing, the sensor configured to provide a sensor output related to movement of the user;
   d. a transducer coupled to the attachment system, the transducer configured to provide outputs to the user; and
   e. a processing unit, having (i) an input, operationally coupled to the sensor output, to receive movement data; (ii) noise filtration processing to remove, from the movement data, noise unrelated to a movement disorder symptom so as to produce a filtered movement signal; (iii) feature extraction processing of the filtered movement signal to characterize features of the filtered movement signal to produce a characterized filtered movement signal; and (iv) processing of the characterized filtered movement signal to produce a stimulation signal output, wherein the stimulation signal output is provided to the transducer which causes the transducer to stimulate the user;
   wherein the processing unit is configured to provide active noise cancellation by transforming the sensor output into the frequency data by applying a Fourier Transform to the sensor output and (i) selecting the fundamental frequency by applying an argmax function to the transformed sensor output and (ii) using a bandpass filter to remove, from the movement data, a set of frequency data outside a specified range associated with the fundamental frequency.

2. The device of claim 1, wherein the processing unit is further configured to provide active noise cancellation by (a) transforming movement data in the time domain into frequency domain data, (b) using the frequency domain data to determine a fundamental frequency of the movement disorder symptoms, (c) generating the stimulation signal output, based on the movement data, having a desired phase shift, relative to a phase of the movement data at the fundamental frequency.

3. The device of claim 2, wherein the sensor includes an inertial motion unit (IMU) configured to calculate acceleration data of the user, and the active noise cancellation processor is further configured to provide active noise cancellation by:
   transforming the acceleration data to the frequency data by applying a Fourier Transform;
   extracting peak frequencies of the acceleration data from the frequency data;
   selecting a window size of the acceleration data based on the peak frequencies; and
   capturing a portion of the sensor output based on the selected window size and inverting the captured portion to generate the stimulation signal.

4. The device of claim 3, wherein in selecting the window size, the processing unit inverts a lowest of the peak frequencies and converts the inverted lowest of the peak frequencies into a time domain.

5. The device of claim 3, wherein the processing unit is configured to set the window size to a fixed value.

6. The device of claim 1, wherein the processing unit is further configured to provide, at the stimulation signal output, a train of stimulation signals, each signal in the train having a distinct set of parameters associated with mitigating the movement disorder symptom and wherein the feature extraction processing includes determining displacement or power data associated with the movement of the user, and the processing unit is also configured to use the displacement or power data to determine which stimulation signal in the train has the greatest mitigation effect.

7. The device according to claim 6, wherein the processing unit is further configured to select the stimulation signal determined to have the greatest mitigation effect for continuous output to the transducer.

8. The device of claim 1, wherein the processing unit is configured to detect and mitigate a movement disorder symptom selected from the group consisting of tremor, rigidity, bradykinesia, dyskinesia, compulsion to move, and combinations thereof.

9. The device of claim 1, wherein the processing unit is configured to detect a freezing gait of a user with Parkinson's Disease.

10. The device of claim 9, wherein the processing unit is further configured to mitigate the freezing gait of the user with Parkinson's Disease by controlling the transducer.

11. The device of claim 1, wherein the attachment system includes a wristband, and a plurality of transducers is distributed throughout a circumference of the wristband.

12. The device of claim 11, wherein the wristband is configured with a hook-and-loop fastener, such that the wristband can be fastened with a single hand for ease of use by those whose fine motor control is affected by a neurological movement disorder.

13. The device of claim 11, wherein the wristband is configured to be expandable via elastic deformation for ease of use by those whose fine motor control is affected by a neurological movement disorder.

14. The device of claim 1, wherein the device is operated by a button on a face of the device, the button being configured to allow for ease of use by a user whose fine motor control is affected by a neurological movement disorder.

15. The device of claim 1, wherein the processing unit is configured to operate in two modes, a first mode to monitor movements of the user passively to detect a movement disorder symptom above a threshold and a second mode, following detection of such a movement disorder symptom, to mitigate the movement disorder symptom.

16. The device of claim 1, further comprising a battery, disposed on the housing, and a magnetic connector coupled to the battery and mounted in the housing for coupling to a mating connector from an external charger, so that the battery can be charged by a user lacking fine motor control.

17. The device of claim 1, wherein the processing unit is further configured to store the movement data in memory coupled to the processing unit.

18. A method for mitigating a movement disorder symptom of a user, the method comprising:
   receiving sensor output related to movement of a user from a sensor;

processing the sensor output to produce a stimulation signal by:
filtering the sensor output to remove noise to produce a filtered signal,
processing the filtered signal by (a) transforming the sensor output into frequency data, (b) using the frequency data to determine a fundamental frequency of a movement disorder symptom, (c) generating the stimulation signal by applying, to the filtered signal, a time delay to produce a desired phase shift at the fundamental frequency, wherein actively processing the filtered signal to transform the sensor output into frequency data includes applying a Fourier Transform to the filtered signal to generate transformed sensor output data and (i) selecting the fundamental frequency by applying an argmax function to the transformed sensor output data and (ii) using a bandpass filter to remove, from the stimulation signal, frequency data outside a specified range associated with the fundamental frequency; and
transmitting the stimulation signal to a transducer coupled to the user to mitigate the set of movement disorder symptoms.

19. A method according to claim 18, wherein the movement disorder symptom is selected from the group consisting of tremor, rigidity, bradykinesia, dyskinesia, compulsion to move, and combinations thereof.

20. A method according to claim 18, wherein receiving sensor output related to movement of the user from a sensor includes operating in two modes, a first mode that monitors movements passively to detect a movement disorder symptom above a threshold and a second mode that, following detection of such a movement disorder symptom, enters into active mitigation of the movement disorder symptom.

21. A method according to claim 18, wherein processing the sensor outputs to produce the stimulation signal further includes:

calculating acceleration data representing acceleration of the user;
transforming the acceleration data to the frequency data by applying a Fourier Transform;
extracting, from the frequency data, peak frequencies of the acceleration data;
selecting a window for the acceleration data based on the peak frequencies; and
capturing a portion of the sensor output based on the selected window and inverting the captured portion to generate the stimulation signal.

22. A method according to claim 21, wherein selecting the window includes inverting a lowest one of the peak frequencies and converting the inverted lowest one of the peak frequencies into a time domain signal.

23. A method according to claim 21, wherein selecting the window includes setting the window to a fixed value.

24. A method of diagnosing a movement disorder in a body part of a susceptible subject comprising:
using a processor, providing a stimulation signal to a transducer in order to induce symptoms of a movement disorder;
applying, through the transducer, the stimulation signal to a user;
receiving movement data, related to movement of the user, from a sensor;
filtering the movement data to remove noise to produce a filtered signal;
processing the filtered signal to (a) transform the movement data into frequency data, (b) use the frequency data to determine a fundamental frequency of the movement of the user, and
processing the frequency data to determine if the user is suffering from the movement disorder.

* * * * *